(12) United States Patent
    Kitano et al.

(10) Patent No.: US 11,249,070 B2
(45) Date of Patent: Feb. 15, 2022

(54) ANTI-CANCER DRUG ASSESSMENT METHOD

(71) Applicant: TOPPAN PRINTING CO., LTD., Taito-ku (JP)

(72) Inventors: Shiro Kitano, Taito-ku (JP); Kei Tsukamoto, Taito-ku (JP); Shinji Irie, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 16/164,989

(22) Filed: Oct. 19, 2018

(65) Prior Publication Data

US 2019/0049432 A1 Feb. 14, 2019

Related U.S. Application Data

(63) Continuation of application No. PCT/JP2017/015804, filed on Apr. 19, 2017.

(30) Foreign Application Priority Data

Apr. 19, 2016 (JP) .............. JP2016-083948
Apr. 19, 2016 (JP) .............. JP2016-083950
Apr. 19, 2016 (JP) .............. JP2016-083951

(51) Int. Cl.
    *G01N 33/50* (2006.01)
    *C12N 5/09* (2010.01)
    *C12N 5/071* (2010.01)

(52) U.S. Cl.
    CPC ....... *G01N 33/5011* (2013.01); *C12N 5/0693* (2013.01); *C12N 5/0697* (2013.01); *G01N 33/5047* (2013.01); *G01N 33/5064* (2013.01); *G01N 33/5085* (2013.01); *C12N 2502/1323* (2013.01); *C12N 2502/28* (2013.01); *C12N 2503/04* (2013.01); *C12N 2513/00* (2013.01); *G01N 2500/10* (2013.01)

(58) Field of Classification Search
    CPC ............. C12N 5/0693; C12N 5/0697; G01N 2500/10; G01N 33/5011; G01N 33/5047; G01N 33/5064; G01N 33/5085; G01N 33/5088
    See application file for complete search history.

(56) References Cited

U.S. PATENT DOCUMENTS

| 2002/0150879 | A1* | 10/2002 | Woltering | .......... | G01N 33/5088 435/4 |
| 2010/0098742 | A1* | 4/2010 | Vacanti | .......... | A61L 27/3604 424/424 |
| 2010/0255528 | A1 | 10/2010 | Zudaire et al. | | |
| 2012/0052524 | A1 | 3/2012 | Kinooka et al. | | |
| 2014/0030257 | A1 | 1/2014 | De La Haba-Rodriguez et al. | | |
| 2015/0111240 | A1 | 4/2015 | Wamhoff et al. | | |

FOREIGN PATENT DOCUMENTS

| JP | 3594978 B | 12/2004 |
| JP | 2008-11797 A | 1/2008 |
| JP | 2012-205516 A | 10/2012 |
| JP | 2014-000038 A | 1/2014 |
| JP | 2014-501918 A | 1/2014 |
| WO | WO 2010/101225 A1 | 9/2010 |
| WO | WO 2015/061372 A1 | 4/2015 |

OTHER PUBLICATIONS

Isella, C., et al., "Stromal contribution to the colorectal cancer transcriptome", Nature Genetics, vol. 47 No. 4, Apr. 2015, pp. 312-319 with cover pages.
Shimoda, M., et al., "Carcinoma-associated fibroblasts are a rate-limiting determinant for tumour progression", Seminars in Cell & Developmental Biology, vol. 21, 2010, pp. 19-25.
Hung, H., "Bevacizumab plus 5-fluorouracil induce growth suppression in the CWR-22 and CWR-22R prostate cancer xenografts", Mol. Cancer Ther, vol. 6 No. 8, Aug. 2007, pp. 2149-2157 with cover page.
Hurkitz, H. Dr., "Bevacizumab plus Irinotecan, Fluorouracil, and Leucovorin for Metastatic Colorectal Cancer", The New England Journal of Medicine, vol. 350 No. 23, Jun. 3, 2004, pp. 2335-2342.
Nishiguchi, A., et al., "Cell-Cell Crosslinking by Bio-Molecular Recognition of Heparin-Based Layer-by-Layer Nanofilms", Macromolecular Bioscience, vol. 15, 2015, pp. 312-317.
Tol, J. Dr., et al., "Chemotherapy, Bevacizumab, and Cetuximab in Metastatic Colorectal Cancer", The New England Journal of Medicine, vol. 360 No. 6, Feb. 5, 2009, pp. 563-572.
Ciardiello, F., et al., "Antiangiogenic and Antitumor Activity of Anti-Epidermal Growth Factor Receptor C225 Monoclonal Antibody in Combination with Vascular Endothelial Growth Factor Antisense Oligonucleotide in Human GEO Colon Cancer Cells", Clinical Cancer Research, vol. 6, Sep. 2000, pp. 3739-3747 with cover page.
Japanese Office Action dated Apr. 6, 2021 in Japanese Patent Application No. 2018-513204 (with English translation), 15 pages.
International Search Report dated Jul. 18, 2017 in PCT/JP2017/015804 filed Apr. 19, 2017, 5 pages.
Hartwell et al., "Niche-based screening identifies small-molecule inhibitors of leukemia stem cells", NIH Public Access Author Manuscript, Nat Chem Biol. Author Manuscript, vol. 9, No. 12, 2013, pp. 840-848, doi:10.1038/nchembio.1367.
Yamazoe, "Fabrication of novel culture system composed of cancer cells and cancer stromal cells for in vitro evaluation of anticancer drugs", Grants-in-Aid for Scientific Research Kenkyu Seika Hokokusho, 2014, 6 pages (with English abstract).

(Continued)

*Primary Examiner* — Blaine Lankford
(74) *Attorney, Agent, or Firm* — Oblon, McClelland, Maier & Neustadt, L.L.P.

(57) ABSTRACT

A method of assessing an anti-cancer drug including culturing a cell structure including cancer cells and stromal cells in a presence of at least one anti-cancer drug, and assessing an anti-cancer effect of the at least one anti-cancer drug based on a number of viable cancer cells in the cell structure after the culturing.

20 Claims, No Drawings

(56) References Cited

OTHER PUBLICATIONS

Xiao et al., "Fibroblasts weaken the anti-tumor effect of gefitinib on co-cultured non-small cell lung cancer cells", Chinese Medical Journal, vol. 127, No. 11, 2014, pp. 2091-2096.
Katt et al., "In Vitro Tumor Models: Advantages, Disadvantages, Variables, and Selecting the Right Platform", Frontiers in Bioengineering and Biotechnology, vol. 4, Article 12, 2016, pp. 1-14.

* cited by examiner

ANTI-CANCER DRUG ASSESSMENT METHOD

CROSS-REFERENCE TO RELATED APPLICATIONS

The present application is a continuation of International Application No. PCT/JP2017/015804, filed Apr. 19, 2017, which is based upon and claims the benefits of priority to Japanese Application No. 2016-083948, filed Apr. 19, 2016, and Japanese Application No. 2016-083950, filed Apr. 19, 2016, and Japanese Application No. 2016-083951, filed Apr. 19, 2016. The entire contents of all of the above applications are incorporated herein by reference.

BACKGROUND OF THE INVENTION

Field of the Invention

The present invention relates to a method for more reliably assessing the anti-cancer effect of an anti-cancer drug in an in vitro system without using animal models. The present invention also relates to a method for accurately assessing in an in vitro system whether higher anti-cancer effects can be obtained by the combined use of an angiogenesis inhibitor and an anti-cancer drug than the use of only an anti-cancer drug without using animal models.

Discussion of the Background

For selection of suitable anti-cancer drugs in the development of anti-cancer drugs or in cancer therapy, the effects of anti-cancer drugs on cancer cells are assessed in an in vitro assay system. The drug approval rate in domestic pharmaceutical companies is as low as only 0.1%. In order to increase the success rate of drug approval, it is necessary to make an early decision on whether drug candidate substances reliably have desired drug efficacy. Highly reliable drug efficacy assessment methods are required. In particular, restrictions of conventional animal models are considered to be one reason that pharmaceutical companies have difficulty in releasing new drugs. Pharmaceutical companies have required drug assessment models that reproduce environments closer to the in vivo environment, in place of animal models.

However, conventional anti-cancer drug assessment methods performed in in vitro systems sometimes give only a low score to drugs that are able to exhibit superior anti-cancer activity when administered into a living body. Thus, there is a problem in that the obtained assessment is not always linked to actual clinical effects. Therefore, conventional in vitro assessment methods sometimes fails to select anti-cancer drugs suitable for cancer therapy, and fails to improve cancer therapy results.

To assess the drug efficacy of anti-cancer drugs, prediction of drug efficacy is performed by genetic testing in the clinical site. For example, KRAS gene mutations in colorectal cancer are a predictive factor for the therapeutic effects of cetuximab. Moreover, EGFR gene mutations in lung cancer are a predictive factor for the therapeutic effects of gefitinib. However, many molecular targeted drug agents are only useable for general gene mutations. Furthermore, there are many somatic mutations that have not yet been identified. Therefore, prediction of drug efficacy by genetic testing may not be sufficient to assess drug efficacy. Furthermore, in the research and development of anti-cancer drugs, even when the efficacy of a drug, among many drugs, was determined by a conventional assessment method, the obtained efficacy assessment did not match the actual clinical results in many cases. This was a serious obstacle to research and development.

As an anti-cancer drug assessment method performed in an in vitro system, for example, PTL 1 discloses a method for performing anti-cancer assessment of drugs by culturing cancer cells coexisting with immune cells in a droplet of collagen gel. This method uses the method disclosed in PTL 2, in which the stroma around cancer cells is actively removed, and the cancer cells are propagated as a cell mass of only cancer cells.

However, data analysis of colorectal cancer patients has recently clarified the possibility that many of genes highly expressed in patients with poor outcome are expressed in stromal cells. Moreover, this possibility was investigated using data obtained from mice implanted with human cancer cells, and it was found that genes highly expressed in patients with poor outcome were not derived from the human cancer tissue, but were derived from the mouse tissue surrounding the human cancer tissue (NPL 1). In particular, it is reported that abnormally activated special fibroblasts often appear in highly malignant cancer. They are called "cancer-associated fibroblasts (CAF)." CAF reportedly promotes angiogenesis, the growth and infiltration of cancer cells, etc. (NPL 2). Accordingly, in the cancer microenvironment (cancer cells and their surrounding environment in the body), the stroma greatly affects cancer cells. It is considered that an environment closer to the in vivo environment can be produced by allowing cancer cells to coexist with the stroma.

In addition to conventionally used general anti-cancer drugs having cytotoxicity, molecular targeted drugs that can exhibit therapeutic effects more specifically on cancer cells and their surrounding tissue (solid tumor) have recently attracted attention as cancer therapy drugs. Of such drugs, angiogenesis inhibitors, such as Avastin (registered trademark) (also known as bevacizumab, produced by Genentech) approved in the U.S. in 2004, are drugs that indirectly exhibit anti-tumor effects by inhibiting the angiogenesis ability of the solid tumor-surrounding tissue to thereby cut the supply of nutrition to the cancer itself, and to reduce the cancer growth rate, unlike conventional anti-cancer drugs that directly exhibit a cytocidal effect.

Angiogenesis inhibitors are drugs that suppress and inhibit angiogenesis by blocking protein signal pathways, essential for blood vessel formation, of factors essential for blood vessel formation or receptors thereof. In therapeutic methods, angiogenesis inhibitors are used not only alone, but also used in combination with conventional anti-cancer drugs having cytotoxicity in many cases. Combination therapy with angiogenesis inhibitors and anti-cancer drugs is more effective than therapy using general anti-cancer drugs having cytotoxicity alone. In Japan, combination therapy methods using antiangiogenic agents and various drugs have been approved for patients with unresectable progressive and recurrent colorectal cancer.

In anti-cancer therapy, therapeutic methods that administer a combination of drugs having different action mechanisms is generally performed, in the expectation of obtaining higher therapeutic effects than use of a single drug. When combined administration is performed, it is preferable to accurately assess how much higher the therapeutic effect obtained by actual combined administration will be, compared with that obtained by use of a single drug. However, as methods for assessing drug efficacy in combination therapy with antiangiogenic agents, in vivo assessment methods in animal models (e.g., mice) and humans are common at present. There is no report on in vitro assessment examples (see, for example, PTL 3, NPL 3, and NPL 4).
PTL 1: JP 2008-11797 A
PTL 2: JP 3594978 B
PTL 3: JP 2014-501918 A
NPL 1: Isella, et al., Nature Genetics, 2015, vol. 47, pp. 312-319
NPL 2: Shimoda, et al., Seminars in Cell & Developmental Biology, 2010, vol. 21 (1), pp. 19-25
NPL 3: Hung, Molecular Cancer Therapeutics, 2007, vol. 6 (8), pp. 2149-2157
NPL 4: Hurwitz, The New England Journal of Medicine, 2004, vol. 350, pp. 2335-2342
NPL 5: Nishiguchi et al., Macromol Bioscience, 2015, vol. 15 (3), pp. 312-317
NPL 6: Tol, et al., The New England Journal of Medicine, 2009, vol. 360 (6), pp. 563-572
NPL 7: Ciardiello, et al., Clinical Cancer Research, 2000, vol. 6, pp. 3739-3747

SUMMARY OF THE INVENTION

According to an aspect of the present invention, a method of assessing an anti-cancer drug includes culturing a cell structure including cancer cells and stromal cells in a presence of at least one anti-cancer drug, and assessing an anti-cancer effect of the at least one anti-cancer drug based on a number of viable cancer cells in the cell structure after the culturing.

DESCRIPTION OF THE EMBODIMENTS

The anti-cancer drug assessment method according to the first embodiment of the present invention will now be described.

The anti-cancer drug assessment method according to the first embodiment of the present invention (hereinafter also referred to as "the assessment method according to the present embodiment") includes a culture step of culturing a cell structure containing cancer cells and cells that constitute a stroma (stromal cells) in the presence of one or more anti-cancer drugs, and an assessment step of assessing the anti-cancer effect of the one or more anti-cancer drugs using, as an indicator, the number of viable cancer cells in the cell structure after the culture step. The assessment method according to the present embodiment assesses anti-cancer effects using a cell structure containing cancer cells in a three-dimensional structure formed from cells that constitute a stroma. The stroma is an important structure in the in vivo cancer microenvironment. Specifically, the in vivo cancer cell environment can be reproduced by incorporating cancer cells into a cell structure having a three-dimensional structure formed by cells that constitute a stroma, and in vivo anti-cancer activity can be appropriately assessed. Therefore, the use of the cell structure enables the assessment of anti-cancer drugs more accurately reflecting human clinical results even in an in vitro assessment system, and highly reliable assessment can be obtained.

<Cell Structure>

In the present specification, the "cell structure" is a three-dimensional structure in which multiple cell layers are laminated. The cell structure used in the present embodiment (hereinafter also referred to as "the cell structure according to the present embodiment") is produced by cancer cells and stromal cells. The cell structure according to the present embodiment may be a cell structure in which cancer cells are scattered in the entire structure, or a cell structure in which cancer cells are present only in a specific layer.

In the assessment method according to the present embodiment, anti-cancer effects can also be assessed using a cell structure in which a stromal cell layer and a cancer cell layer are divided by a semipermeable membrane so as to allow the contact of components secreted from the stromal cells that form a three-dimensional structure. That is, the cell structure according to the present embodiment may be a cell structure in which a layer containing cancer cells and a layer containing stromal cells are divided by a semipermeable membrane. In the cell structure, the layer containing cancer cells may be a single layer or a multilayer. Similarly, the layer containing stromal cells may be a single layer or a multilayer. Moreover, the cell layer containing stromal cells may be a layer formed only from one or more types of stromal cells, or a layer containing cells other than stromal cells. Similarly, the cell layer containing cancer cells may be a layer formed only from cancer cells, or a layer containing cells other than cancer cells.

Due to the use of a cell structure in which stromal cells are formed into a three-dimensional structure, such as in vivo stromal tissue, and components secreted from the stromal cells are able to contact cancer cells through a semipermeable membrane, the same environment as a cancer cell environment under the influence of in vivo stromal tissue can be reproduced, and in vivo anti-cancer activity can be appropriately assessed. Therefore, the use of the cell structure enables the assessment of anti-cancer drugs more accurately reflecting human clinical results even in an in vitro assessment system, and highly reliable assessment can be obtained.

When cancer cells are obtained from a cancer patient, many fibroblasts are also obtained together with cancer cells; however, it is difficult to separate the cancer cells and the fibroblasts. Examples of the method for removing fibroblasts from cancer tissue obtained from a cancer patient include a method in which all the cells of the cancer tissue are cultured in a serum-free medium to kill fibroblasts, and then fibroblast masses and cancer cells are separated by a semipermeable membrane. However, cancer cells lose cell-cell contact after passing through a semipermeable membrane, and there is a concern that normal drug assessment cannot be performed.

Accordingly, in many cases, a cell population containing cancer cells obtained from a cancer patient is similarly labeled regardless of the cell type, and then used for the production of cell structures. However, it is difficult to label cancer cells in distinction from fibroblasts; thus, when many fibroblasts are contained in a cell population obtained from a cancer patient, drug efficacy may be mistakenly assessed. In particular, since the cell structure used in the present embodiment contains many stromal cells, it is necessary to accurately assess drug effects on cancer cells targeted by drugs. In the assessment method according to the present embodiment, stromal cells that constitute a layer containing stromal cells, and stromal cells derived from a cancer patient, are separated by a semipermeable membrane so that they are not mixed; thus, even if a cell structure contains many stromal cells together with cancer cells, the influence of the stromal cells derived from the cancer patient is suppressed, and more reliable assessment can be obtained.

Examples of stromal cells include endothelial cells, fibroblasts, nerve cells, dendritic cells, macrophages, mast cells, epithelial cells, cardiac muscle cells, liver cells, islet cells, tissue stem cells, smooth muscle cells, and the like. The cell structure according to the present embodiment may contain one type of stromal cell, or two or more types of stromal cells. The cell type of stromal cells contained in the cell structure according to the present embodiment is not limited, and can be suitably selected in consideration of the origin and type of cancer cells to be contained, the type of anti-cancer drug used for assessment, the in vivo environment in which the target anti-cancer activity is exhibited, etc.

The vascular network structure and the lymphatic network structure are important for the growth and activation of cancer cells. Accordingly, the cell structure according to the present embodiment preferably has a vascular network structure. That is, the cell structure according to the present embodiment is preferably one in which at least one vascular network structure of lymph vessels and blood vessels is three-dimensionally formed in a cell laminate in which vessels are not formed, to produce tissue closer to in vivo tissue. A vascular network structure may be formed only in the cell structure, or may be formed so that at least part of the vascular network structure is exposed to the surface or bottom of the cell structure. In the present specification, the term "vascular network structure" refers to a net-like structure, such as a vascular network or lymphatic network, in body tissue.

A vascular network structure can be formed by incorporating endothelial cells, which constitute vessels, as stromal cells. The endothelial cells contained in the cell structure according to the present embodiment may be vascular endothelial cells or lymphatic endothelial cells. Moreover, both vascular endothelial cells and lymphatic endothelial cells may be contained.

When the cell structure according to the present embodiment has a vascular network structure, the cells other than endothelial cells in the cell structure are not limited, as long as they do not inhibit the endothelial cells from forming a vessel network. However, cells that constitute surrounding tissue of vessels in a living body are preferable, because the endothelial cells can easily form a vessel network maintaining the original function and shape. Furthermore, a cell structure at least containing fibroblasts as cells other than endothelial cells is more preferable, because a microenvironment closer to the in vivo cancer microenvironment can be obtained. Even more preferable are a cell structure containing vascular endothelial cells and fibroblasts, a cell structure containing lymphatic endothelial cells and fibroblasts, and a cell structure containing vascular endothelial cells, lymphatic endothelial cells, and fibroblasts. The cells other than endothelial cells contained in the cell structure may be derived from the same organism species as that of the endothelial cells, or from different organism species. Moreover, the cell structure may contain, other than endothelial cells, one type of cell, or two or more types of cells.

The number of endothelial cells in the cell structure according to the present embodiment is not limited, as long as the number of endothelial cells is sufficient for forming a vascular network structure. The number of endothelial cells can be suitably determined in consideration of the size of the cell structure, the type of endothelial cells, the type of cells other than endothelial cells, etc. For example, a cell structure in which a vascular network structure is formed can be prepared by setting the abundance ratio (cell number ratio) of endothelial cells to all the cells that constitute the cell structure according to the present embodiment to 0.1% or more. When fibroblasts are used as the cells other than endothelial cells, the number of endothelial cells in the cell structure according to the present embodiment is preferably 0.1% or more, more preferably 0.1 to 10.0%, and even more preferably 0.1 to 5.0%, of the number of fibroblasts. When both vascular endothelial cells and lymphatic endothelial cells are contained as endothelial cells, the total number of vascular endothelial cells and lymphatic endothelial cells is preferably 0.1% or more, more preferably 0.1 to 10.0%, and even more preferably 0.1 to 5.0%, of the number of fibroblasts.

The cancer cells contained in the cell structure according to the present embodiment may be established culture cells, or cancer cells obtained from a cancer patient. The cancer cells obtained from a cancer patient may be previously grown by culture. Specific examples thereof include primary cancer cells obtained from a cancer patient, artificially cultured cancer cells, iPS cancer stem cells, cancer stem cells, and established cancer cells previously prepared for use in studies of cancer therapy and development of anti-cancer drugs. Moreover, the cancer cells may be derived from a human or an animal other than a human. When the cell structure according to the present embodiment contains cancer cells obtained from a cancer patient, cells other than the cancer cells obtained from the cancer patient may be contained together with the cancer cells. Examples of the cells other than cancer cells include one or more types of cells contained in solid tissue removed after surgery.

Cancer cells are cells that are derived from somatic cells and that acquire infinite proliferation potential. Non-limiting examples of the cancer from which cancer cells are derived include breast cancer (e.g., invasive ductal carcinoma, ductal carcinoma in situ, and inflammatory breast cancer), prostate cancer (e.g., hormone-dependent prostate cancer and hormone-independent prostate cancer), pancreatic cancer (e.g., pancreatic duct cancer), gastric cancer (e.g., papillary adenocarcinoma, mucinous adenocarcinoma, and adenosquamous carcinoma), lung cancer (e.g., non-small-cell lung cancer, small-cell lung cancer, and malignant mesothelioma), colon cancer (e.g., gastrointestinal stromal tumor), rectal cancer (e.g., gastrointestinal stromal tumor), colorectal cancer (e.g., familial colorectal cancer, hereditary nonpolyposis colorectal cancer, and gastrointestinal stromal tumor), small intestinal cancer (e.g., non-Hodgkin's lymphoma and gastrointestinal stromal tumor), esophageal cancer, duodenal cancer, tongue cancer, pharyngeal cancer (e.g., nasopharyngeal cancer, oropharynx cancer, and hypopharyngeal cancer), head and neck cancer, salivary gland cancer, brain tumor (e.g., pineal astrocytoma, pilocytic astrocytoma, diffuse astrocytoma, and anaplastic astrocytoma), neurilemmoma, liver cancer (e.g., primary liver cancer and extrahepatic bile duct cancer), renal cancer (e.g., renal cell cancer and transitional cell cancer of the renal pelvis and ureter), gallbladder cancer, bile duct cancer, pancreatic cancer, hepatoma, endometrial cancer, cervical cancer, ovarian cancer (e.g., epithelial ovarian cancer, extragonadal germ cell tumor, ovarian germ cell tumor, and ovarian low-malignant potential tumor), bladder cancer, urethral cancer, skin cancer (e.g., intraocular (ocular) melanoma and Merkel cell carcinoma), hemangioma, malignant lymphoma (e.g., reticulosarcoma, lymphosarcoma, and Hodgkin's disease), melanoma (malignant melanoma), thyroid cancer (e.g., medullary thyroid cancer), parathyroid cancer, nasal cancer, paranasal cancer, bone tumor (e.g., osteosarcoma, Ewing's tumor, uterine sarcoma, and soft-tissue sarcoma), metastatic medulloblastoma, hemangiofibroma, dermatofibrosarcoma protuberans, retinal sarcoma, penile cancer, testicular tumor, pediatric solid cancer (e.g., Wilms tumor and pediatric renal tumor), Kaposi sarcoma, Kaposi sarcoma caused by AIDS, tumor of maxillary sinus, fibrous histiocytoma, leiomyosarcoma, rhabdomyosarcoma, chronic myeloproliferative disorders, leukemia (e.g., acute myelogenous leukemia and acute lymphoblastic leukemia), and the like.

The type of cells, such as stromal cells and cancer cells, which constitute the cell structure according to the present embodiment, is not limited. The cells may be cells obtained from an animal, cells obtained by culturing cells obtained from an animal, cells obtained by subjecting cells obtained from an animal to various treatments, or cultured cell lines. In the case of cells obtained from an animal, the sampling site is not limited. The cells may be somatic cells derived from the bone, muscle, viscus, nerve, brain, skin, blood, etc.; reproductive cells; or embryonic stem cells (ES cells). Moreover, the organism species from which the cells constituting the cell structure according to the present embodiment are derived is not limited. For example, usable cells can be derived from humans or animals, such as monkeys, dogs, cats, rabbits, pigs, cows, mice, and rats. The cells obtained by culturing cells obtained from an animal may be primary cultured cells or subcultured cells. Examples of cells that have been subjected to various treatments include induced pluripotent stem cells (iPS cells), cells after differentiation induction, and the like. The cell structure according to the present embodiment may be composed of only cells derived from the same organism species, or cells derived from several types of organism species.

The number of cancer cells in the cell structure according to the present embodiment is not limited; however, in the case of a cell structure in which cancer cells and stromal cells coexist, the ratio of the number of endothelial cells to the number of cancer cells ([number of endothelial cells]/[number of cancer cells]) in the cell structure is preferably more than 0 and 1.5 or less, because a microenvironment closer to the in vivo cancer microenvironment can be obtained. Moreover, when a cell structure containing endothelial cells, fibroblasts, and cancer cells is used, the ratio of the number of fibroblasts to the number of cancer cells ([number of fibroblasts]/[number of cancer cells]) in the cell structure is preferably 0.6 to 100, and more preferably 50 to 100.

The size and shape of the cell structure according to the present embodiment are not limited. Because it is possible to form a vascular network structure in a state closer to vessels formed in in vivo tissue, and to obtain more highly accurate assessment, the thickness of the cell structure is preferably 5 μm or more, more preferably 10 μm or more, even more preferably 50 μm or more, and still more preferably 100 μm or more. The thickness of the cell structure is preferably 500 μm or less, more preferably 400 μm or less, and even more preferably 300 μm or less. The number of cell layers in the cell structure according to the present embodiment is preferably about 2 to 60, more preferably about 5 to 60, and even more preferably about 10 to 60.

When the cell structure according to the present embodiment is a cell structure in which a stromal cell layer and a cancer cell layer are divided by a semipermeable membrane, the thickness of the layer containing stromal cells in the cell structures is preferably 5 μm or more, more preferably 10 μm or more, even more preferably 50 μm or more, and still more preferably 100 μm or more. Moreover, the thickness of the layer containing stromal cells in the cell structures is preferably 500 μm or less, more preferably 400 μm or less, and even more preferably 300 μm or less. In this case, the number of cell layers in the cell structure is also preferably about 2 to 60, more preferably about 5 to 60, and even more preferably about 10 to 60.

In the present specification, the number of cell layers that constitute the cell structure is measured by diving the total number of cells that constitute a three-dimensional structure by the number of cells per layer (the number of cells necessary to form one layer). The number of cells per layer can be examined in such a manner that cells are previously cultured on a plane so that they are confluent in a cell container that is used in the production of a cell structure. Specifically, the number of cell layers in a cell structure formed in a certain cell container can be calculated by counting the total number of cells that constitute the cell structure, and dividing the total number of cells by the number of cells per layer in the cell container.

The semipermeable membrane for dividing the layer containing stromal cells and the layer containing cancer cells may be a membrane that allows components with a relatively small molecular weight, such as water, protein, nucleic acid, lipid, and sugar, to freely pass therethrough, but does not allow cells to freely transfer. Such a membrane enables the formation of a cell structure in which components secreted from stromal cells can freely pass through the membrane, and a cell layer containing stromal cells and a cell layer containing cancer cells are maintained in a state where these layers are separated but partially contacted. In this case, the semipermeable membrane contained in the cell structure is, for example, a membrane with a pore size of 0.4 μm to 8 μm.

The material of the semipermeable membrane contained in the cell structure is not limited, as long as it does not inhibit the growth and activity of cancer cells and stromal cells. Examples of the semipermeable membrane include porous membranes formed from regenerated cellulose (cellophane), acetyl cellulose, polyacrylonitrile, polytetrafluoroethylene, polyester-based polymer alloy, polysulfone, or the like.

In general, the cell structure according to the present embodiment is produced in a cell culture container. The cell culture container is not limited, as long as it enables the production of a cell structure and enables the culture of the produced cell structure. Specific examples of the cell culture container include dishes, cell culture inserts (e.g., Transwell (registered trademark) inserts, Netwell (registered trademark) inserts, Falcon (registered trademark) cell culture inserts, and Millicell (registered trademark) cell culture inserts), tubes, flasks, bottles, plates, and the like. In the production of the cell structure according to the present embodiment, dishes or various cell culture inserts are preferable, because they can more appropriately perform assessment using the cell structure.

The cell structure according to the present embodiment may be a structure formed from multiple cell layers containing cancer cells and stromal cells, and the method for producing the cell structure is not limited. For example, the method may be a production method including sequentially laminating each layer, a method including forming two or more cell layers at once, or a method including forming multiple cell layers by suitably combining both production methods. Moreover, the cell structure according to the present embodiment may be a multilayer structure in which the type of cell that constitutes each layer is different for each layer, or the type of cell that constitutes each layer is the same in the all layers of the structure. For example, the method used may be a production method in which a layer is formed for every type of cell, the resulting cell layers are sequentially laminated, or a method in which a cell mixed solution containing a mixture of several types of cells is previously prepared, and a multilayer cell structure is produced at once from the cell mixed solution.

As the production method for sequentially laminating each layer, for example, the method disclosed in JP 4919464 B can be used. Specifically, this method continuously laminates cell layers by repeating a step of forming a cell layer and a step of bringing the formed cell layer into contact with a solution containing an extracellular matrix (ECM) component. For example, when this method is performed, a cell mixture containing all cells that constitute a cell structure is previously prepared, and each cell layer is formed from this cell mixture, thereby producing a cell structure in which a vascular network structure is formed in the entire structure, and cancer cells are scattered in the entire structure. Furthermore, cell layers may be formed for each cell type, thereby producing a cell structure in which a vascular network structure is formed only in a layer formed from endothelial cells, and cancer cells are present only in a specific layer.

Moreover, for example, when the above method is performed, a cell mixture containing all cells that constitute a layer containing stromal cells, and a cell mixture containing all cells that constitute a layer containing cancer cells is separately prepared in advance. Then, the cell mixture containing stromal cells is first laminated sequentially to form a cell layer containing a single layer or a multilayer, a semipermeable membrane is then placed on the cell layer, and the cell mixture containing cancer cells is laminated on the semipermeable membrane to thereby form a cell layer. This enables the production of a cell structure in which a vascular network structure is formed in the entire cell layer containing stromal cells, and cancer cells are scattered in the entire cell layer containing cancer cells. Furthermore, cell layers containing stromal cells are formed for each cell type, thereby producing a cell structure in which a vascular network structure is formed only in a layer containing endothelial cells, and cancer cells are present only in a layer divided from stromal cells by a semipermeable membrane.

As the method for forming two or more cell layers at once, for example, the method disclosed in JP 5850419 B can be used. Specifically, this method produces a cell structure having multiple cell layers by previously coating the entire cell surface with a polymer containing an arginine-glycine-aspartic acid (RGD) sequence bound to integrin, and a polymer interacting with the polymer containing the RGD sequence, accommodating the cells coated with an adhesive film in a cell culture container, and then integrating the coated cells by centrifugation or the like.

For example, when this method is performed, it is possible to use coated cells prepared by previously preparing a cell mixture containing all cells that constitute a cell structure, and adding an adhesive component to the cell mixture. This enables the production of a cell structure in which cancer cells are scattered in the entire structure by one centrifugation. Similarly, a cell structure in which a vascular network structure is formed in the entire structure can be produced by one centrifugation using coated cells prepared by previously preparing a cell mixture containing all cells that constitute the cell structure, and adding an adhesive component to the cell mixture. Moreover, it is also possible to, for example, separately prepare coated cells of endothelial cells, coated cells of fibroblasts, and coated cells of a cell population obtained from a cancer patient, form a multilayer composed of the coated cells of fibroblasts, then laminate one layer formed from the coated cells of endothelial cells thereon, further laminate a multilayer formed from the coated cells of fibroblasts thereon, and further laminate one layer formed from the coated cells of the cells containing cancer cells thereon. This enables the production of a cell structure having a vascular network structure inserted between thick fibroblast layers, and having, on a top surface thereof, a layer containing cancer cells obtained from a cancer patient.

Furthermore, it is also possible to, for example, separately prepare coated cells of endothelial cells, coated cells of fibroblasts, and coated cells of a cell population obtained from a cancer patient, form a multilayer from the coated cells of fibroblasts, laminate one layer formed from the coated cells of endothelial cells thereon, further laminate a multilayer formed from the coated cells of fibroblasts thereon, further place a semipermeable membrane thereon, and laminate one layer formed from the coated cells of the cells containing cancer cells on the semipermeable membrane. This enables the production of a cell structure having a vascular network structure inserted between thick fibroblast layers, and having a layer containing cancer cells obtained from a cancer patient divided from a fibroblast layer by a semipermeable membrane.

The cell structure according to the present embodiment can also be produced by a method including the following steps (a) to (c):
(a) a step of obtaining a mixture by mixing cells and an extracellular matrix component in a cationic buffer;
(b) a step of seeding the mixture obtained at step (a) in a cell culture container; and
(c) a step of removing a liquid component from the cell mixture in the cell culture container after step (b), and obtaining a cell structure in which the cells are laminated in multiple layers in the cell culture container.

In step (a), cells are mixed with an extracellular matrix component and a buffer containing a cationic substance, and cell aggregates are formed from the cell mixture, thereby obtaining a three-dimensional cell tissue with few large voids therein. Because the obtained three-dimensional cell tissue is relatively stable, the cell tissue can be cultured at least for several days, and the tissue is substantially undamaged during medium replacement.

Furthermore, step (b) can also include precipitating, in a cell culture container, the cell mixture seeded in the cell culture container. The cell mixture may be actively precipitated by centrifugal separation or the like, or may be spontaneously precipitated.

In step (a), it is preferable to further mix the cells with a strong polyelectrolyte. When the cells are mixed with a cationic substance, a strong polyelectrolyte, and an extracellular matrix component, a thick three-dimensional cell tissue with few voids can be obtained even when the cells are spontaneously precipitated, without requiring treatment, such as centrifugal separation, for actively gathering the cells in step (b).

Examples of the cationic buffer include tris-hydrochloric acid buffers, tris-maleic acid buffers, bis-tris buffers, HEPES, and the like. The concentration and pH of the cationic substance in the cationic buffer (e.g., tris in a tris-hydrochloric acid buffer) are not limited, as long as they do not adversely affect the cell growth and the production of the cell structure. For example, the concentration of the cationic substance in the cationic buffer is 10 to 100 mM, preferably 40 to 70 mM, and more preferably 50 mM. Moreover, the pH of the cationic buffer is 6.0 to 8.0, preferably 6.8 to 7.8, and more preferably 7.2 to 7.6.

Examples of the strong polyelectrolyte include glycosaminoglycans, such as heparin, chondroitin sulfate (e.g., chondroitin 4-sulfate and chondroitin 6-sulfate), heparan sulfate, dermatan sulfate, keratan sulfate, and hyaluronic acid; dextran sulfate, rhamnan sulfate, fucoidan, carrageenan, polystyrene sulfonate, polyacrylamide-2-methylpropane sulfonic acid, polyacrylic acid, derivatives thereof, and the like. The mixture prepared in step (a) may be mixed with only one strong polyelectrolyte, or two or more strong polyelectrolytes in combination. In the production of the cell structure according to the present embodiment, it is preferable to use glycosaminoglycans, and it is more preferable to use heparin, dextran sulfate, chondroitin sulfate, or dermatan sulfate. In the production of the cell structure according to the present embodiment, it is even more preferable to use heparin. The amount of strong polyelectrolyte mixed in the cationic buffer is not limited, as long as it does not adversely affect the cell growth and the production of the cell structure. For example, the concentration of the strong polyelectrolyte in the cationic buffer is more than 0 mg/mL and less than 1.0 mg/mL, preferably 0.025 to 0.1 mg/mL, and more preferably 0.05 to 0.1 mg/mL. Derivatives of the above polyelectrolytes may also be used, as long as they do not adversely affect the cell growth and the formation of cell aggregates. Moreover, in one aspect of the present embodiment, a cell structure can be produced by preparing the above mixture without mixing a strong electrolyte mentioned above.

Examples of the extracellular matrix component include collagen, laminin, fibronectin, vitronectin, elastin, tenascin, entactin, fibrillin, proteoglycan, modified forms or variants thereof, and the like. Examples of proteoglycans include chondroitin sulfate proteoglycan, heparan sulfate proteoglycan, keratan sulfate proteoglycan, dermatan sulfate proteoglycan, and the like. The extracellular matrix component used in the present embodiment is preferably collagen, laminin, or fibronectin; collagen is particularly preferable. Modified forms and variants of the extracellular matrix components mentioned above may also be used, as long as they do not adversely affect the cell growth and the formation of cell aggregates. The mixture prepared in step (a) may be mixed with only one extracellular matrix component, or two or more extracellular matrix components in combination. In the production of the cell structure according to the present embodiment, it is preferable to use collagen, laminin, or fibronectin; and it is particularly preferable to use collagen. The amount of extracellular matrix component mixed in the cationic buffer is not limited, as long as it does not adversely affect the cell growth and the production of the cell structure. For example, the concentration of the extracellular matrix component in the cationic buffer is more than 0 mg/mL and less than 1.0 mg/mL, preferably 0.025 to 0.1 mg/mL, and more preferably 0.05 to 0.1 mg/mL.

The mixing ratio of the strong polyelectrolyte to the extracellular matrix component mixed in the cationic buffer is 1:2 to 2:1. In the production of the cell structure according to the present embodiment, the mixing ratio of the strong polyelectrolyte to the extracellular matrix component is preferably 1:1.5 to 1.5:1, and more preferably 1:1.

A cell structure with sufficient thickness can be produced by repeating steps (a) to (c). Specifically, the following process is repeated: as step (b), the mixture prepared in step (a) is seeded on the cell structure obtained in a previous step (c), and step (c) is then performed. The cell composition of the mixture newly seeded on the cell structure obtained in step (c) may be the same or different from the cell composition that constitutes the already produced cell structure.

For example, first, a mixture containing only fibroblasts as cells is prepared in step (a), and steps (b) and (c) are performed to obtain a cell structure formed from 10 fibroblast layers in a cell culture container. Subsequently, as step (a), a mixture containing only vascular endothelial cells as cells is prepared, and steps (b) and (c) are performed to laminate one vascular endothelial cell layer on the fibroblast layers in the cell culture container. Furthermore, as step (a), a mixture containing only fibroblasts as cells is prepared, and steps (b) and (c) are performed to laminate 10 fibroblast layers on the vascular endothelial cell layer in the cell culture container. In addition, as step (a), a mixture containing cancer cells obtained from a cancer patient is prepared, and steps (b) and (c) are performed to laminate one cancer cell layer on the fibroblast layers in the cell culture container. This enables the production of a cell structure in which 10 fibroblast layers, 1 vascular endothelial cell layer, 10 fibroblast layers, and 1 cancer cell layer are sequentially laminated in layers for each cell type. The thickness and number of cell layers laminated in step (c) can be adjusted by controlling the number of cells seeded in step (b). The number of cell layers laminated in step (c) increases as a larger number of cells is seeded in step (b). Moreover, a mixture containing all of the fibroblasts for 20 fibroblast layers and the vascular endothelial cells for 1 vascular endothelial cell layer is prepared in step (a), steps (b) and (c) are performed to laminate a mixture containing cancer cells obtained from a cancer patient prepared in the same manner as described above on the formed multilayer structure, thereby producing a cell structure having a thickness corresponding to the 21 layers, in which a cancer cell layer is laminated on the structure having a vascular network structure scattered therein. Furthermore, a mixture containing all of the fibroblasts for 20 fibroblast layers, the vascular endothelial cells for 1 vascular endothelial cell layer, and the cells derived from a cancer patient for 1 cancer cell layer is prepared in step (a), then steps (b) and (c) are performed, thereby producing a cell structure having a thickness corresponding to the 22 layers, in which the cancer cells and a vascular network structure are both independently scattered in the structure.

When a cell structure in which a stromal cell layer and a cancer cell layer are divided by a semipermeable membrane is produced, for example, a mixture containing only fibroblasts as cells is first prepared in step (a), and steps (b) and (c) are performed to obtain a cell structure formed from 10 fibroblast layers in a cell culture container. Subsequently, as step (a), a mixture containing only vascular endothelial cells as cells is prepared, and steps (b) and (c) are performed to laminate one vascular endothelial cell layer on the fibroblast layers in the cell culture container. Furthermore, as step (a), a mixture containing only fibroblasts as cells is prepared, and steps (b) and (c) are performed to laminate 10 fibroblast layers on the vascular endothelial cell layer in the cell culture container, after which a semipermeable membrane is placed thereon. Furthermore, as step (a), a mixture containing cancer cells obtained from a cancer patient is prepared, and steps (b) and (c) are performed to laminate one cancer cell layer on the semipermeable membrane in the cell culture container. This enables the production of a cell structure in which 10 fibroblast layers, 1 vascular endothelial cell layer, 10 fibroblast layers, a semipermeable membrane, and 1 cancer cell layer are sequentially laminated in layers for each cell type. The thickness and number of cell layers laminated in step (c) can be adjusted by controlling the number of cells seeded in step (b). The number of cell layers laminated in step (c) increases as a larger number of cells is seeded in step (b). Moreover, a mixture containing all of the fibroblasts for 20 fibroblast layers and the vascular endothelial cells for 1 vascular endothelial cell layer is prepared in step (a), then steps (b) and (c) are performed, a semipermeable membrane is placed on the formed multilayer structure, and a mixture containing cancer cells obtained from a cancer patient prepared in the same manner as described above is laminated on the semipermeable membrane, thereby producing a cell structure having a thickness corresponding to the 21 layers, in which a cancer cell layer is laminated, through a semipermeable membrane, on the structure having a vascular network structure scattered therein.

When steps (a) to (c) are repeated, the obtained cell structure may be cultured after step (c) and before the following step (b). The culture conditions, such as the composition of the culture medium used for culture, culture temperature, culture time, and atmospheric composition during culture, are determined to be suitable for the culture of the cells that constitute the cell structure. Examples of the culture medium include D-MEM, E-MEM, MEMα, RPMI-1640, Ham's F-12, and the like.

After step (a), the following steps (a'-1) and (a'-2) may be performed, and then step (b) may be performed: (a'-1) a step of removing a liquid part from the obtained mixture, and obtaining cell aggregates, and (a'-2) a step of suspending the cell aggregates in a solution.

Moreover, after step (a), the following steps (b'-1) and (b'-2) may be performed in place of step (b). In the present specification, the term "cell viscous body" refers to gel-like cell aggregates as described in NPL 5.

(b'-1) a step of seeding the mixture obtained at step (a) in a cell culture container, and then removing a liquid component from the mixture to obtain a cell viscous body; and (b'-2) a step of suspending the cell viscous body in a solvent in the cell culture container. A desired tissue body can be obtained by carrying out the above steps (a) to (c); however, a more uniform tissue body can be obtained by carrying out steps (a'-1) and (a'-2) after step (a), and then carrying out step (b).

The solvent for preparing a cell suspension is not limited, as long as it does not have toxicity to the cells, and does not impair proliferative properties or function. Water, buffers, cell culture media, etc., can be used. Examples of buffers include phosphate-buffered saline (PBS), HEPES, Hanks' buffers, and the like. Examples of culture media include D-MEM, E-MEM, MEMα, RPMI-1640, Ham's F-12, and the like.

The following step (c') may be performed in place of step (c).

(c') a step of removing a liquid component from the seeded mixture, and forming a cell layer on the substrate.

The method for removing the liquid component in steps (c) and (c') is not limited, as long as it does not adversely affect the cell growth and the production of the cell structure. The method for removing a liquid component from a suspension of the liquid component and a solid component can be suitably performed by a method known to a person skilled in the art. Examples of the method include centrifugal separation, magnetic separation, filtration, and the like.

For example, when a cell culture insert is used as the cell culture container, the cell culture insert in which the mixture is seeded can be subjected to centrifugal separation at 10° C. at 400×g for 1 minute to thereby remove the liquid component.

<Anti-Cancer Drug>

The anti-cancer drugs used in the assessment method according to the present embodiment may be drugs used for cancer therapy, and include not only drugs that directly act on cancer cells, such as drugs having cytotoxicity, but also drugs that do not have cytotoxicity but suppress the growth of cancer cells, etc. Examples of anti-cancer drugs that do not have cytotoxicity include: drugs that do not directly attack cancer cells, but exhibit the function to suppress the growth of cancer cells, blunt the activity of cancer cells, or kill cancer cells, by the cooperative action with in vivo immune cells or other drugs; and drugs that suppress the growth of cancer cells by impairing cells, other than cancer cells, and tissue. The anti-cancer drugs used in the present embodiment may be known drugs having anti-cancer activity, or candidate compounds for novel anti-cancer drugs.

The anti-cancer drugs having cytotoxicity are not limited. Examples thereof include molecular targeted drugs, alkylating agents, antimetabolites represented by 5-FU-based anti-cancer drugs, plant alkaloids, anti-cancer antibiotics, platinum derivatives, hormonal agents, topoisomerase inhibitors, microtubule inhibitors, and compounds classified into biological response modifiers.

The anti-cancer drugs not having cytotoxicity are not limited. Examples thereof include angiogenesis inhibitors, prodrugs of anti-cancer drugs, drugs that regulate intracellular metabolism enzyme activity associated with the metabolism of anti-cancer drugs or prodrugs thereof (hereinafter referred to as "intracellular enzyme regulators" in the specification), immunotherapy agents, and the like. Other examples include drugs that are finally involved in anti-cancer activity by increasing the function of anti-cancer drugs or improving the in vivo immune function.

The angiogenesis inhibitors may be compounds that are expected to have angiogenesis inhibitory activity, and may be known angiogenesis inhibitors or candidate compounds for novel angiogenesis inhibitors. Examples of known angiogenesis inhibitors include Avastin, EYLEA, Suchibaga, CYRAMZA (registered trademark) (also known as ramucirumab, produced by Eli Lilly), BMS-275291 (produced by Bristol-Myers), Celecoxib (produced by Pharmacia/Pfizer), EMD121974 (produced by Merck), Endostatin (produced by EntreMed), Erbitaux (produced by ImClone Systems), Interferon-α (produced by Roche), LY317615 (produced by Eli Lilly), Neovastat (produced by Aeterna Laboratories), PTK787 (produced by Abbott), SU6688 (produced by Sugen), Thalidomide (produced by Celgene), VEGF-Trap (produced by Regeneron), Iressa (registered trademark) (also known as gefitinib, produced by AstraZeneca), Caplerusa (registered trademark) (also known as vandetanib, produced by AstraZeneca), Recentin (registered trademark) (also known as cediranib, produced by Astra-Zeneca), VGX-100 (produced by Circadian Technologies), VD1 and cVE199, VGX-300 (produced by Circadian Technologies), sVEGFR2, hF4-3C5, Nexavar (registered trademark) (also known as sorafenib, produced by Bayer Yakuhin), Vortrient (registered trademark) (also known as pazopanib, produced by GlaxoSmithKline), Sutent (registered trademark) (also known as sunitinib, produced by Pfizer), Inlyta (registered trademark) (also known as axitinib, produced by Pfizer), CEP-11981 (produced by Teva Pharmaceutical Industries), AMG-386 (also known as trebananib, produced by Takeda Yakuhin), anti-NRP2B (produced by Genentech), Ofev (registered trademark) (also known as nintedanib, produced by Boehringer Ingelheim), AMG706 (also known as motesanib, produced by Takeda Yakuhin), and the like.

Prodrugs of anti-cancer drugs are drugs that are converted into activators having anti-cancer activity by organs, such as the liver, and intracellular enzymes of cancer cells. Cytokine networks enhance enzyme activity to thereby increase the number of activators, and result in the enhancement of anti-tumor effects; thus, these prodrugs are exemplified as drugs involved in anti-cancer activity.

Examples of intracellular enzyme regulators include gimeracil, which does not have a direct anti-tumor effect when used alone, but is involved in anti-cancer activity by inhibiting a degrading enzyme (dihydropyrimidine dehydrogenase: DPD) of 5-FU-based anti-cancer drugs.

Examples of immunotherapy agents include drugs used for biological response modifier therapy, such as krestin, lentinan, and OK-432 (hereinafter abbreviated as "BRM preparations"); cytokine-based preparations, such as interleukins and interferons; and the like.

In the assessment method according to the present embodiment, one anti-cancer drug may be used, or two or more anti-cancer drugs may be used in combination. Furthermore, one or more anti-cancer drugs may be used in combination with drugs other than anti-cancer drugs. For example, when an anti-cancer drug that exhibits an anti-cancer effect when used alone is administered in combination with other drugs in actual clinical practice, the assessment method according to the present embodiment may be performed using the anti-cancer drug in combination with the other drugs.

In the assessment method according to the present embodiment, the effect of combined use of an anti-cancer drug having cytotoxicity and an angiogenesis inhibitor can also be assessed using, as the cell structure, a cell structure containing multilayer cells in which a vascular network structure is formed, and some of the component cells are cancer cells, and using the anti-cancer drug having cytotoxicity and the angiogenesis inhibitor as anti-cancer drugs.

Because this method uses a cell structure having a vascular network structure in a three-dimensional structure closer to the in vivo state, drug efficacy obtained by the combined use of an angiogenesis inhibitor and an anti-cancer drug can be accurately assessed, without using animal models.

The anti-cancer drugs having cytotoxicity may be compounds that are expected to have cytotoxicity, and may be known anti-cancer drugs or candidate compounds for novel anti-cancer drugs.

Specifically, the assessment method according to the present embodiment includes a culture step of culturing a cell structure containing cancer cells and having a vascular network structure in the presence of an angiogenesis inhibitor and an anti-cancer drug having cytotoxicity, and an assessment step of assessing the anti-cancer effect of combined use of the angiogenesis inhibitor and the anti-cancer drug using, as an indicator, the number of viable cancer cells in the cell structure after the culture step.

The cell structure has a vascular network structure, and is composed of endothelial cells that constitute vessels, and cells that do not constitute vessels (cells other than endothelial cells).

The type of cells other than endothelial cells contained in the cell structure is not limited, as long as they do not inhibit the endothelial cells form forming a vessel network. The cell type can be suitably selected in consideration of the origin and type of cancer cell to be contained, the types of angiogenesis inhibitor and anti-cancer drug used for assessment, the in vivo environment where the target anti-cancer activity is exhibited, and the like.

<Culture Step>

In the assessment method according to the present embodiment, as the culture step, a cell structure containing cancer cells and stromal cells is first cultured in the presence of one or more anti-cancer drugs. Specifically, the cell structure is cultured in a culture medium containing one or more anti-cancer drugs. When the effect of combined use of an anti-cancer drug having cytotoxicity and an angiogenesis inhibitor is assessed, a cell structure having a vascular network structure is cultured in the presence of the angiogenesis inhibitor and the anti-cancer drug, as the culture step. Specifically, the cell structure is cultured in a culture medium containing the angiogenesis inhibitor and the anti-cancer drug.

The amount of anti-cancer drug mixed in the culture medium can be experimentally determined in consideration of the culture conditions, such as the type and number of cells constituting the cell structure, the type and amount of cancer cells contained, the type of culture medium, culture temperature, and culture time. The culture time is not limited. For example, the culture time is 24 to 96 hours, preferably 48 to 96 hours, and more preferably 48 to 72 hours. Furthermore, hydrodynamic loads, such as reflux, may be applied, if necessary, within a range that does not greatly change the culture environment.

<Assessment Step>

The anti-cancer effect of an anti-cancer drug is assessed using, as an indicator, the number of viable cancer cells in the cell structure after the culture step. Specifically, when the number of viable cancer cells is larger than that when culture is performed in the absence of the anti-cancer drug, the anti-cancer drug is assessed to have an anti-cancer effect on the cancer cells contained in the cell structure. In contrast, when the number of viable cancer cells is equal or significantly larger than that when culture is performed in the absence of the anti-cancer drug, the anti-cancer drug is assessed to have no anti-cancer effect on the cancer cells contained in the cell structure.

When the effect of combined use of an anti-cancer drug having cytotoxicity and an angiogenesis inhibitor is assessed, the number of viable cancer cells in the cell structure after the culture step is used as an indicator to assess the anti-cancer effect of combined use of the angiogenesis inhibitor and the anti-cancer drug. Specifically, when the number of viable cancer cells is larger than that when culture is performed in the presence of the anti-cancer drug alone, it is assessed that a higher anti-cancer effect is obtained by using the anti-cancer drug and the angiogenesis inhibitor in combination, rather than using the anti-cancer drug alone; that is, it is assessed that an effect of combined use is obtained. In contrast, when the number of viable cancer cells is equal to that when culture is performed in the presence of the anti-cancer drug alone, it is assessed that a higher anti-cancer effect is not obtained by using the anti-cancer drug and the angiogenesis inhibitor in combination, rather than using the anti-cancer drug alone; that is, it is assessed that an effect of combined use is not obtained. Furthermore, when the number of viable cancer cells is significantly larger than that when culture is performed in the presence of the anti-cancer drug alone, it is assessed that the anti-cancer effect is rather reduced by using the anti-cancer drug in combination with the angiogenesis inhibitor.

The number of viable cancer cells can be assessed using a signal correlated with the number of viable cancer cells or the abundance thereof. It is only necessary that the number of viable cancer cells at the time of assessment can be measured; it is not always necessary to measure cancer cells in a living state. For example, cancer cells are labeled so that they are distinguished from other cells, and a signal from the label can be examined as an indicator. For example, cancer cells living in the cell structure can be directly counted by fluorescently labeling cancer cells, and then determining the cell viability. In this case, an image analysis technique can also be used. The cell viability can be determined by a known cell viability determination method, such as trypan blue staining or propidium iodide (PI) staining. The fluorescent labeling of cancer cells can be performed by a known method, such as immunostaining, which uses, for example, an antibody against a substance specifically expressed on the cell surface of cancer cells as a primary antibody, and a fluorescently-labeled secondary antibody capable of specifically binding to the primary antibody. The determination of cell viability and the measurement of the number of viable cells may be performed using intact cell structures or in a state where the cell structure is destroyed at the single-cell level. For example, after the three-dimensional structure of the cell structure after labeling of cancer cells and dead cells is destroyed, only the number of cancer cells living at the time of assessment can be directly counted by fluorescence activated cell sorting (FACS) or the like using the label as an indicator.

The number of viable cancer cells in the cell structure can also be measured with time by labeling cancer cells living in the cell structure, and detecting with time a signal from the label. The cancer cells in the cell structure may be labeled after the cell structure is produced, or cancer cells may be previously labeled before the cell structure is produced. For example, when a cell structure containing a cell population containing cancer cells derived from a cancer patient is used, the cancer cells can be previously labeled before the cell structure is produced. Moreover, together with the cancer cells, other cells derived from the cancer patient may also be similarly labeled. In addition, when cancer cells that constantly express fluorescent dyes are used, the number of viable cancer cells can be assessed by measuring, with a microplate reader or the like, the fluorescence intensity of a lysate obtained by dissolving the cell structure.

Moreover, in the case of a cell structure in which a cancer cell layer and a stromal cell layer are divided by a semipermeable membrane, cancer cells can be easily separated from stromal cells and collected. The number of viable cells among the collected cancer cells can be measured by a viable cell count measurement method known in this technical field, such as the MTT method.

The assessment method according to the present embodiment uses a cell structure having a stroma similar to a tissue structure surrounding cancer cells in an actual living body, wherein components secreted from the stroma affect the cancer cells. Furthermore, it is also possible to use a cell structure having, in addition to a stroma, a vascular network structure similar to the vasculature in an actual living body. Thus, in the assessment method according to the present embodiment, assessment is performed in an environment reproduced in vitro closer to the in vivo environment; therefore, highly reliable assessment of drug efficacy can be obtained. Anti-cancer drugs that are assessed to have anti-cancer effects by the assessment method according to the present embodiment can be expected to exhibit sufficient anti-cancer effects when they are actually administered to cancer patients. Similarly, the combination of an angiogenesis inhibitor and an anti-cancer drug having cytotoxicity assessed to have an effect of combined use by the assessment method according to the present embodiment can be expected to exhibit an anti-cancer effect higher than that of the use of only the anti-cancer drug when they are actually administered to cancer patients. Accordingly, the assessment method according to the present embodiment can be used as an unprecedented in vitro drug assessment tool, for example, in screening or drug-repositioning screening of anti-cancer drug candidate compounds in the drug design field, or in screening and determination (anti-cancer drug sensitivity test) of anti-cancer drug therapy (use of one drug or combined use of drugs) in the clinical field. In particular, anti-cancer drugs that are assessed to have anti-cancer effects by the assessment method according to the present embodiment performed using a cell structure containing cancer cells obtained from a cancer patient can be expected to exhibit suitable anti-cancer effects when they are actually administered to the cancer patient.

The anti-cancer drug assessment kit according to the second embodiment of the present invention (hereinafter also referred to as "the kit according to the present embodiment") contains a cell structure containing at least cells containing a stroma, and includes a cell culture container for accommodating the cell structure. The assessment method according to the above first embodiment can be performed more simply by using an anti-cancer drug assessment kit obtained by forming, into a kit, the reagents etc., used in the assessment method according to the first embodiment. For example, the cell structure contained in the kit according to the present embodiment may be a cell structure that does not contain cancer cells and has a vascular network structure. The thickness of the cell structure contained in the kit is preferably 5 μm or more.

The cell structure contained in the kit according to the present embodiment may be a cell structure containing cancer cells; however, the kit may contain a cell structure that does not contain cancer cells, but contains cells that constitute a stroma, and a cancer cell layer may be formed on the surface of the cell structure immediately before the assessment method is actually performed. Furthermore, the kit may contain, in place of the cell structure, cells other than cancer cells among the cells that constitute the cell structure.

The cell structure contained in the kit according to the present embodiment contains at least a stroma, and may contain a semipermeable membrane on a top surface thereof. The cell structure contained in the kit may be one in which a cancer cell layer is laminated on a semipermeable membrane; however, the kit may contain a cell structure that does not contain cancer cells, and that has a semipermeable membrane placed on a cell layer containing stromal cells, and a cancer cell layer may be formed on the semipermeable membrane of the cell structure immediately before the assessment method is actually performed.

The kit may further contain other substances used in the assessment method. Examples of the other substances include anti-cancer drugs, culture media for the cell structure, labeling substances for labeling cancer cells, cell viability test reagents, substances used in the production of the cell structure (e.g., cationic buffers, strong polyelectrolyte, and extracellular matrix components), and the like.

Furthermore, when an anti-cancer drug having cytotoxicity and an antiangiogenic agent are used in combination as anti-cancer drugs, the effect of combined use of the anti-cancer drug having cytotoxicity and the angiogenesis inhibitor can be assessed more simply.

EXAMPLES

Examples of the present invention are described in detail in the Examples below; however, the present invention is not limited to the following Examples.

Example 1 Production of Cell Structure Having Vasculature

Cell structures formed from fibroblasts and vascular endothelial cells and having a vascular network structure were produced, and the vascular network structure was observed.

The cell structures having a vascular network structure used herein were cell structures formed from two types of cells, i.e., normal human dermal fibroblasts (NHDF) (CC-2509, produced by Lonza) and human umbilical vein endothelial cells (HUVEC) (CC-2517A, produced by Lonza). The cell culture container used was a Transwell cell culture insert (product number: #3470, produced by Corning), and the culture media used were 10 volume % bovine serum (EXO-FBS-50A-1, produced by System Biosciences) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The anti-angiogenic agent to be assessed was bevacizumab (product number: MAB293, produced by R&D Systems).

<Production of Cell Structure>

First, $2 \times 10^6$ NHDF and HUVEC with a content of 0.05, 0.1, 0.25, 0.5, 1.0, 1.5, or 5.0% of the number of NHDF cells were suspended in a tris-hydrochloric acid buffer containing heparin and collagen (0.1 mg/mL heparin, 0.1 mg/mL collagen, and 50 mM tris; pH: 7.4) to prepare cell suspensions (the ratio of the number of HUVEC to the number of NHDF:5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 96 hours (step (c)).

<Fluorescent Labeling of Cells Constituting Blood Vessels, and Assessment>

Fluorescence immunostaining was performed on the cell structures after culture using an anti-CD31 antibody (product number: JC70A M082329, produced by DAKO) and a secondary antibody (product number: A-11001, produced by Invitrogen), and the blood vessels in the structures were labeled with a green fluorescent dye. The fluorescence-labeled cell structures were directly observed, and the presence of vascular network formation was confirmed.

TABLE 1

| HUVEC content (%) | Formation of vascular network |
| --- | --- |
| 0.05 | Not formed |
| 0.1 | Formed |
| 0.25 | Formed |
| 0.5 | Formed |
| 1.0 | Formed |
| 1.5 | Formed |
| 5.0 | Formed |

As shown in Table 1, the formation of vascular network structures was confirmed under all the conditions, except for the case where the HUVEC content was 0.05% of the number of NHDF.

Example 2

The anti-cancer effect of an anti-cancer drug, doxorubicin, was assessed using cell structures formed from fibroblasts, vascular endothelial cells, and cancer cells, and having a vascular network structure.

The cell structures containing cancer cells and having a vascular network structure used herein were cell structures in which a cancer cell layer formed from human colon cancer cell line HT29 (ATCC Number: HTB-38TM) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The anti-cancer drug to be assessed was doxorubicin (product number: 046-21523, produced by Wako Pure Chemical Industries, Ltd.).

<Production of Cell Structure>

First, NHDF alone or a mixture of NHDF and HUVEC was suspended in a tris-hydrochloric acid buffer containing heparin and collagen (0.1 mg/mL heparin, 0.1 mg/mL collagen, and 50 mM tris; pH: 7.4) to prepare cell suspensions (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)). Then, the Transwell cell culture insert was centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 24 hours (step (c)).

After $2 \times 10^4$ cancer cells suspended in a suitable amount of culture medium were seeded in the Transwell cell culture insert in which the structures were formed, the Transwell cell culture insert was centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 96 hours. After termination of the culture, cell structures in which a cancer cell layer was laminated on a layer having a vascular network structure were obtained. The cancer cells used were previously fluorescently labeled (product number: PKH67GL, produced by SIGMA).

<Culture in the Presence of Doxorubicin>

The obtained cell structures were cultured in a culture medium with a doxorubicin final concentration of 10 μM at 37° C. with 5% $CO_2$ for 72 hours. As a control, the cell structures were cultured in the same manner as described above, except that doxorubicin was not added (culture in the absence of the drug).

Moreover, for comparison, in place of the above cell structures, structures were constructed by culturing cancer cells so as to form a single layer in a general culture container (2D method), and the resulting 2D cultures were similarly cultured in the presence of doxorubicin. A vascular network was not formed in the obtained 2D cultures even when cancer cells and vascular endothelial cells were made to coexist.

<Dispersion of Cell Structure>

Next, a suitable amount of tris buffer solution (50 mM, pH: 7.4) was added to the Transwell cell culture insert, and the liquid component was then removed. This series of processes was repeated 3 times. Subsequently, 300 μL of 0.25% trypsin-EDTA solution (produced by Invitrogen) was added to the Transwell cell culture insert, and incubation was performed in a $CO_2$ incubator (37° C., 5% $CO_2$) for 15 minutes. Thereafter, all of the solution was collected, and transferred to a 1.5-mL collection tube to which 300 μL of 0.25% trypsin-EDTA solution (produced by Invitrogen) had been previously added. Then, 100 μL of 0.25% trypsin-EDTA solution (produced by Invitrogen) was added to the Transwell cell culture insert, and incubation was performed, together with the 1.5-mL collection tube, in a $CO_2$ incubator (37° C., 5% $CO_2$) for 5 minutes. Thereafter, all of the solution was collected, and transferred to a 1.5-mL collection tube. Then, 300 μL of 0.25% trypsin-EDTA solution (produced by Invitrogen) was added, and incubation was performed in a $CO_2$ incubator (37° C., 5% $CO_2$) for 5 minutes, thereby obtaining a cell structure dispersion.

<Viable Cell Count Analysis and Assessment>

After the obtained cell structure dispersions were each immersed in a trypan blue solution for trypan blue staining, the number of cells emitting fluorescence and not stained with trypan blue was counted as the number of viable cancer cells. The cell count was performed using a cell counter "Countess II" (produced by Life Technologies) in fluorescence mode.

Furthermore, the 2D cultures were similarly stained with trypan blue, and the number of viable cancer cells was counted. Measurements were repeated three times for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

Table 2 shows the calculated CNT results of each culture, together with the number of constituting cells. In the table, the "2D" row shows the results of the 2D cultures, and the "3D" row shows the results of the produced cell structures (the cell structures of the present Example).

TABLE 2

| Structure | Cell | | | CNT (%) | |
| --- | --- | --- | --- | --- | --- |
| | NHDF | HUVEC | HT29 | Average value | S.D. |
| 2D | — | — | $2 \times 10^4$ | 6.87 | 0.75 |
| | — | $2 \times 10^4$ | $2 \times 10^4$ | 21.40 | 3.37 |
| | $2 \times 10^4$ | — | $2 \times 10^4$ | 13.20 | 3.28 |
| 3D | $2 \times 10^6$ | — | $2 \times 10^4$ | 29.77 | 3.88 |
| | $1 \times 10^6$ | $3 \times 10^4$ | $2 \times 10^4$ | 28.22 | 1.86 |
| | $2 \times 10^6$ | $3 \times 10^4$ | $2 \times 10^4$ | 31.22 | 4.21 |

Among the produced cell structures, a vascular network structure was not formed in the cell structure formed from only NHDF and HT29 (NHDF (20 layers)-HT29 (1 layer)), whereas a vascular network structure was formed in the cell structures containing HUVEC. These cell structures showed similar CNT values, regardless of whether a vascular network was formed. It was revealed that whether a vascular network was formed did not affect the assessment of the anti-cancer effect of cytotoxic anti-cancer drugs, such as doxorubicin.

In contrast, the 2D cultures showed markedly lower CNT than that of the cell structures of the present Example, and had higher doxorubicin sensitivity. In particular, the CNT of the cell structures of the present Example was at least about 5 times higher than that of the 2D culture containing only cancer cells, and the 2D culture containing only cancer cells and fibroblasts. It was suggested that the cell structures of the present Example constructed an environment in which the drug was at least about five times less effective than in the 2D cultures. Interestingly, it was found that the anti-cancer drug was about two times more effective in the 2D culture co-cultured with fibroblasts than in the 2D culture co-cultured with vascular endothelial cells. In general, the biggest reason that anti-cancer drug assessment by 2D culture method is not popular is that drugs are too effective; however, in the assessment method of the present Example using the cell structures of the present Example, excess influence of the drug was suppressed. It was revealed that more reliable and stable assessment was possible.

Example 3

The anti-cancer effect of an anti-cancer drug, doxorubicin, was assessed using a cell structure in which a vascular network structure was formed in a layer shape, and a cell structure in which a vascular network structure was scattered in the entire structure.

The cell culture container, culture media, and doxorubicin used herein were the same as those used in Example 2.

<Production of Cell Structure in which Vascular Network Structure is Scattered in the Entire Structure>

A cell structure was produced in the same manner as in Example 2, except that $2 \times 10^6$ NHDF and $3 \times 10^4$ HUVEC were suspended in a tris-hydrochloric acid buffer containing heparin and collagen. In the obtained cell structure, a cancer cell layer was laminated on a layer in which a vascular network structure was scattered in the entire structure (mixed layer (21 layers) of NHDF (20 layers) and HUVEC (1 layer)-HT29 (1 layer)).

<Production of Cell Structure in which Vascular Network Structure is Formed in Layer Shape>

First, $1 \times 10^6$ NHDF was suspended in a tris-hydrochloric acid buffer containing heparin and collagen (0.1 mg/mL heparin, 0.1 mg/mL collagen, and 50 mM Tris; pH: 7.4) to prepare cell suspensions (step (a)). These cell suspensions were each centrifuged at room temperature at 400×g for 1 minute, the supernatant was removed, and then the cell suspension was resuspended in a suitable amount of culture medium (steps (a'-1) and (a'-2)). Furthermore, $3 \times 10^4$ HUVEC was suspended in a tris-hydrochloric acid buffer containing heparin and collagen (0.1 mg/mL heparin, 0.1 mg/mL collagen, and 50 mM tris; pH: 7.4) to prepare cell suspensions (step (a)). These cell suspensions were each centrifuged at room temperature at 400×g for 1 minute, the supernatant was removed, and then the cell suspension was resuspended in a suitable amount of culture medium (steps (a'-1) and (a'-2)).

Subsequently, NHDF ($1 \times 10^6$ cells) was seeded in a Transwell cell culture insert, and centrifuged at room temperature at 400×g for 1 minute to remove the liquid component. Next, HUVEC ($3 \times 10^4$ cells) was seeded, and centrifuged at room temperature at 400×g for 1 minute to remove the liquid component. Finally, NHDF ($1 \times 10^6$ cells) was seeded (step (b)), and centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 24 hours (step (c)).

Then, $2\times10^4$ HT29 cells were laminated on the formed structure and cultured in the same manner as in Example 2. After termination of the culture, a cell structure having a cancer cell layer laminated on a structure in which a vascular network structure was formed in a layered shape (NHDF (10 layers)-HUVEC (1 layer)-NHDF (10 layers)-HT29 (1 layer)) was obtained.

<Culture in the Presence of Doxorubicin>

The obtained cell structures were cultured in a culture medium with a doxorubicin final concentration of 10 μM at 37° C. with 5% $CO_2$ for 72 hours. As a control, the cell structures were cultured in the same manner as described above, except that doxorubicin was not added (culture in the absence of the drug).

<Dispersion of Cell Structure, Viable Cell Count Analysis, and Assessment>

After the cell structures were each dispersed in the same manner as in Example 2, and the obtained dispersions were stained with trypan blue, the number of viable cancer cells was counted to calculate CNT (%). Measurements were repeated three times for each culture condition. Table 3 shows the results.

TABLE 3

| Structure | CNT (%) Average value | S.D. |
|---|---|---|
| Cell structure in which a vascular network structure is formed in a layer shape | 31.22 | 4.21 |
| Cell structure in which a vascular network structure is scattered in the entire structure | 31.06 | 1.88 |

When any cell structure was used, CNT was almost equal. Whether a vascular network structure was formed in a layer shape or scattered in the structure did not particularly affect the drug effect of doxorubicin.

Example 4

Among anti-cancer drugs, the effect of combined use of an antiangiogenic agent, bevacizumab, and a molecular targeted drug having cytotoxicity, cetuximab, was assessed using cell structures formed from fibroblasts (NHDF), vascular endothelial cells (HUVEC), and cancer cells (HT29), and having a vascular network structure.

The cell culture container and culture media used herein were the same as those used in Example 2. The anti-cancer drugs to be assessed were bevacizumab (product number: MAB293, produced by R&D Systems) and cetuximab (no model number, produced by Merck Serono).

<Production of Cell Structure>

Cell structures were produced in the same manner as in "Cell structure in which vascular network structure is scattered in the entire structure" in Example 3.

<Culture in the Presence of Bevacizumab and/or Cetuximab>

The obtained cell structures were cultured in a culture medium in which the amount of bevacizumab added per well of the Transwell cell culture insert was 0 or 2 μg, and the final concentration of cetuximab was 0 or 1 mg/mL, at 37° C. with 5% $CO_2$ for 72 hours. As a control, the cell structures were cultured in the same manner as described above, except that bevacizumab and cetuximab were not added (culture in the absence of the drugs).

Moreover, for comparison, in place of the above cell structures, structures were produced by culturing cancer cells so as to form a single layer in a general culture container (2D method), and spheroids were produced by spheroid culture of a mixture of $2\times10^6$ NHDF, $3\times10^4$ HUVEC, and $2\times10^4$ HT29 (spheroid method). These were similarly cultured in the presence of bevacizumab and cetuximab.

<Dispersion of Cell Structure, Viable Cell Count Analysis, and Assessment>

After the cell structures were each dispersed in the same manner as in Example 2, and the obtained dispersions were stained with trypan blue, the number of viable cancer cells was counted to calculate CNT (%). Measurements were repeated three times for each culture condition. Results are shown in Table 4.

In the table, the "2D" row shows the results of the 2D cultures, the "Spheroid" row shows the results of the spheroids, and the "3D" row shows the results of the produced cell structures.

TABLE 4

| | Drug | | CNT (%) | | |
|---|---|---|---|---|---|
| Structure | Cetuximab | Bevacizumab | Average value | Median value | S.D. |
| 2D | 1 mg/mL | — | 62.1 | 60.5 | 2.73 |
| | — | 2 μg | 93.9 | 99.3 | 20.14 |
| | 1 mg/mL | 2 μg | 56.7 | 55.5 | 2.11 |
| Spheroid | 1 mg/mL | — | 64.9 | 61.2 | 6.41 |
| | — | 2 μg | 108.6 | 113.8 | 23.73 |
| | 1 mg/mL | 2 μg | 54.3 | 52.1 | 16.38 |
| 3D | 1 mg/mL | — | 70.4 | 69.4 | 4.41 |
| | — | 2 μg | 105.2 | 112.7 | 27.17 |
| | 1 mg/mL | 2 μg | 105.8 | 109.0 | 19.44 |

As a result, the CNT of the 2D cultures and spheroids was about 100% when bevacizumab was administered alone, and there was no anti-cancer effect; however, their CNT was as low as about 60% when cetuximab was administered alone, and when cetuximab and bevacizumab were administered in combination. Thus, an anti-cancer effect was observed. In contrast, the CNT of the cell structures of the present Example was low when cetuximab was administered alone, and an anti-cancer effect was observed; however, their CNT was about 100% when bevacizumab was administered alone, and when cetuximab and bevacizumab were administered in combination. Thus, there was no anti-cancer effect.

NPL 6 reports that, as a result of a randomized clinical test in which chemotherapy combining bevacizumab (Avastin) and cetuximab (Erbitux) was compared with chemotherapy using bevacizumab alone, the non-recurrent survival time and total median survival time of patients were shortened by the addition of cetuximab in actual clinical tests. However, NPL 7 reports that the effect of combined use of bevacizumab and cetuximab was more effective than single-drug therapy in patient-derived xenograft (PDX) animal models. That is, this combined use example is an example in which human clinical test results could not be predicted by drug efficacy assessment using animal models. However, as shown in Table 3, when the cell structures of the present Example were used, administration of cetuximab alone was effective, while combined use with bevacizumab was not effective. These results were the same as the results of the human clinical tests described in NPL 6. This suggested the possibility that the assessment method according to an embodiment of the present invention using a cell structure containing stromal tissue having a three-dimensional structure can more accurately predict human clinical results than animal models.

Example 5

The effect of combined use of an antiangiogenic agent, bevacizumab, and an anti-cancer drug, 5-FU, was assessed using cell structures formed from fibroblasts (NHDF), vascular endothelial cells (HUVEC), and cancer cells (HT29 or HCT116), and having a vascular network structure.

The cell structures containing cancer cells and having a vascular network structure used herein were cell structures in which a cancer cell layer formed from HT29 or HCT116 (ATCC Number: CCL-247) was laminated on a top surface of a multilayer structure formed from two types of cells, i.e., NHDF and HUVEC. The cell culture container and culture media used herein were the same as those used in Example 2.

The antiangiogenic agent to be assessed was bevacizumab (product number: MAB293, produced by R&D Systems), and the general cytotoxic anti-cancer drug used was 5-FU (product number: 064-01403, produced by Wako Pure Chemical Industries, Ltd.).

<Production of Cell Structure>

First, $2 \times 10^6$ NHDF and $3 \times 10^4$ HUVEC were suspended in a tris-hydrochloric acid buffer containing heparin and collagen (0.1 mg/mL heparin, 0.1 mg/mL collagen, and 50 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)). Then, the Transwell cell culture insert was centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 24 hours (step (c)).

After $2 \times 10^4$ cancer cells suspended in a suitable amount of culture medium were seeded in the Transwell cell culture insert in which the structure was formed (step (b)), the Transwell cell culture insert was centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 96 hours (step (c)). After termination of the culture, a cell structure having a cancer cell layer laminated on a layer having a vascular network structure (mixed layer (21 layers) of NHDF (20 layers) and HUVEC (1 layer)-cancer cells (1 layer)) was obtained. The cancer cells used were previously fluorescently labeled (product number: PKH67GL, produced by SIGMA).

<Culture in the Presence of Bevacizumab and 5-FU>

The obtained cell structures were cultured in a culture medium in which the amount of bevacizumab added per well of the Transwell cell culture insert was 0 or 2 µg, and the final concentration of 5-FU was 100 µm or 1 mM, at 37° C. with 5% $CO_2$ for 72 hours. As a control, the cell structures were cultured in the same manner as described above, except that bevacizumab and 5-FU were not added (culture in the absence of the drugs).

Moreover, for comparison, in place of the above cell structures, structures were produced by culturing cancer cells so as to form a single layer in a general culture container (2D method), and spheroids were produced by spheroid culture of a mixture of $2 \times 10^6$ NHDF, $3 \times 10^4$ HUVEC, and $2 \times 10^4$ cancer cells (spheroid method). These were similarly cultured in the presence of bevacizumab and 5-FU. A vascular network structure was not confirmed in the 2D cultures obtained by the 2D method.

<Dispersion of Cell Structure, Viable Cell Count Analysis, and Assessment>

After the cell structures were each dispersed in the same manner as in Example 2, and the obtained dispersions were stained with trypan blue, the number of viable cancer cells was counted to calculate CNT (%).

Furthermore, the 2D cultures and the spheroids were also similarly stained with trypan blue, and the number of viable cancer cells was counted. Measurements were repeated three times for each culture condition.

TABLE 5

| HT29 Structure | Drug | | CNT (%) | |
|---|---|---|---|---|
| | 5-FU | Bevacizumab | Average value | S.D. |
| 2D | 100 µM | — | 54.2 | 28.94 |
| | 100 µM | 2 µg | 54.2 | 18.06 |
| | 1 mM | — | 25.8 | 5.28 |
| | 1 mM | 2 µg | 25.8 | 5.28 |
| Spheroid | 100 µM | — | 57.5 | 38.88 |
| | 100 µM | 2 µg | 57.5 | 5.01 |
| | 1 mM | — | 44.8 | 31.64 |
| | 1 mM | 2 µg | 46.0 | 34.79 |
| 3D | 100 µM | — | 97.6 | 11.32 |
| | 100 µM | 2 µg | 67.6 | 11.48 |
| | 1 mM | — | 75.0 | 14.98 |
| | 1 mM | 2 µg | 52.6 | 5.45 |

TABLE 6

| HCT116 Structure | Drug | | CNT (%) | |
|---|---|---|---|---|
| | 5-FU | Bevacizumab | Average value | S.D. |
| 2D | 100 µM | — | 38.9 | 2.81 |
| | 100 µM | 2 µg | 39.1 | 5.86 |
| | 1 mM | — | 15.3 | 5.12 |
| | 1 mM | 2 µg | 15.3 | 5.12 |
| Spheroid | 100 µM | — | 62.3 | 2.52 |
| | 100 µM | 2 µg | 61.7 | 2.08 |
| | 1 mM | — | 27.7 | 1.15 |
| | 1 mM | 2 µg | 29.1 | 2.14 |
| 3D | 100 µM | — | 86.9 | 8.67 |
| | 100 µM | 2 µg | 69.5 | 10.90 |
| | 1 mM | — | 61.2 | 4.82 |
| | 1 mM | 2 µg | 33.3 | 2.57 |

Table 5 shows the CNT results calculated when HT29 cells were used as the cancer cells, and Table 6 shows the CNT results calculated when HCT116 cells were used as the cancer cells. In the table, the "2D" row shows the results of the 2D cultures, the "Spheroid" row shows the results of the spheroids, and the "3D" row shows the results of the produced cell structures.

For both types of cancer cells, the CNT of the 2D cultures and spheroids was almost equal between the use of only 5-FU (culture conditions in the presence of 5-FU alone) and the combined use with bevacizumab (culture conditions in the presence of both 5-FU and bevacizumab), and there was no significant difference in drug sensitivity (anti-cancer effect). In contrast, when the cell structures of the present Example were used (the assessment method of the present Example), CNT was markedly lower, for any cancer cells, in the combined use with bevacizumab than in the use of only 5-FU, regardless of the 5-FU concentration. The combined use with bevacizumab significantly increased drug sensitivity, and an effect of combined use was confirmed.

Example 6

The effect of combined use of an antiangiogenic agent, bevacizumab, and an anti-cancer drug, oxaliplatin, was assessed using cell structures formed from fibroblasts, vascular endothelial cells, and cancer cells, and having a vascular network structure.

The cell structures containing cancer cells and having a vascular network structure used herein were the cell structures produced in Example 5, and the cell culture container, culture media, and bevacizumab used herein were also the same as those used in Example 5.

<Culture in the Presence of Bevacizumab and Oxaliplatin>

The obtained cell structures were cultured in a culture medium in which the amount of bevacizumab added per well of the Transwell cell culture insert was 0 or 2 μg, and the final concentration of oxaliplatin (produced by Pfizer Inc.) was 10 or 100 μg/mL, at 37° C. with 5% $CO_2$ for 72 hours. As a control, the cell structures were cultured in the same manner as described above, except that bevacizumab and oxaliplatin were not added (culture in the absence of the drugs).

<Dispersion of Cell Structure, Viable Cell Count Analysis, and Assessment>

After the cell structures were each dispersed in the same manner as in Example 2, and the obtained dispersions were stained with trypan blue, the number of viable cancer cells was counted to calculate CNT (%).

Moreover, for comparison, 2D cultures and spheroids were also cultured in the presence of bevacizumab and oxaliplatin in the same manner as in Example 5, and CNT (%) was calculated.

TABLE 7

| HT29 Structure | Drug | | CNT (%) | |
|---|---|---|---|---|
| | Oxaliplatin | Bevacizumab | Average value | S.D. |
| 2D | 10 μg/mL | — | 39.4 | 8.75 |
| | 10 μg/mL | 2 μg | 38.3 | 2.00 |
| | 100 μg/mL | — | 16.0 | 2.92 |
| | 100 μg/mL | 2 μg | 16.4 | 2.29 |
| Spheroid | 10 μg/mL | — | 48.2 | 6.41 |
| | 10 μg/mL | 2 μg | 46.8 | 3.65 |
| | 100 μg/mL | — | 22.3 | 5.55 |
| | 100 μg/mL | 2 μg | 25.5 | 16.93 |
| 3D | 10 μg/mL | — | 63.6 | 4.42 |
| | 10 μg/mL | 2 μg | 47.4 | 4.25 |
| | 100 μg/mL | — | 31.9 | 6.05 |
| | 100 μg/mL | 2 μg | 22.3 | 1.64 |

TABLE 8

| HCT116 Structure | Drug | | CNT (%) | |
|---|---|---|---|---|
| | Oxaliplatin | Bevacizumab | Average value | S.D. |
| 2D | 10 μg/mL | — | 23.8 | 5.67 |
| | 10 μg/mL | 2 μg | 24.4 | 1.11 |
| | 100 μg/mL | — | 11.3 | 0.81 |
| | 100 μg/mL | 2 μg | 12.3 | 3.32 |
| Spheroid | 10 μg/mL | — | 51.8 | 10.21 |
| | 10 μg/mL | 2 μg | 50.5 | 3.38 |
| | 100 μg/mL | — | 18.8 | 2.30 |
| | 100 μg/mL | 2 μg | 20.3 | 3.54 |
| 3D | 10 μg/mL | — | 54.1 | 11.07 |
| | 10 μg/mL | 2 μg | 45.9 | 12.73 |
| | 100 μg/mL | — | 35.6 | 5.12 |
| | 100 μg/mL | 2 μg | 22.0 | 3.00 |

Table 7 shows the CNT results calculated when HT29 cells were used as the cancer cells, and Table 8 shows the CNT results calculated when HCT116 cells were used as the cancer cells.

For both type of cancer cells, the CNT of the 2D cultures and spheroids was almost equal between the use of only oxaliplatin (culture conditions in the presence of oxaliplatin alone) and the combined use with bevacizumab (culture conditions in the presence of both oxaliplatin and bevacizumab), and there was no significant difference in drug sensitivity. In contrast, when the cell structures of the present Example were used, CNT was markedly lower, for any cancer cells, in the combined use with bevacizumab than in the use of only oxaliplatin, regardless of the oxaliplatin concentration. The combined use with bevacizumab significantly increased drug sensitivity, and an effect of combined use was confirmed.

Example 7

The effect of combined use of an antiangiogenic agent, bevacizumab, and an anti-cancer drug, oxaliplatin, was assessed using cell structures produced under different conditions for forming a vascular network structure.

The cell culture container, culture media, and bevacizumab used herein were the same as those used in Example 5, and the oxaliplatin used herein was the same as that used in Example 6. Furthermore, HT29 cells were used as the cancer cells.

<Production of Cell Structure>

Cell structures were produced in the same manner as in Example 5, except that the ratio of the number of HUVEC to the number of NHDF (HUVEC content) was changed to 0.05, 0.25, 0.5, or 1.5%.

As a result, a vascular network structure was formed in the cell structures produced with a HUVEC content of 0.25, 0.5, or 1.5%, whereas a vascular network structure was not formed in the cell structure produced with a HUVEC content of 0.05%.

<Culture in the Presence of Bevacizumab and Oxaliplatin>

The obtained cell structures were cultured in a culture medium in which the amount of bevacizumab added per well of the Transwell cell culture insert was 0 or 2 μg, and the final concentration of oxaliplatin was 100 μg/mL, at 37° C. with 5% $CO_2$ for 72 hours. As a control, the cell structures were cultured in the same manner as described above, except that bevacizumab and oxaliplatin were not added (culture in the absence of the drugs).

<Dispersion of Cell Structure, Viable Cell Count Analysis, and Assessment>

After the cell structures were each dispersed in the same manner as in Example 2, and the obtained dispersions were stained with trypan blue, the number of viable cancer cells was counted to calculate CNT (%). Measurements were repeated three times for each culture condition.

TABLE 9

| HUVEC content (%) | Drug | Formation of vascular network | CNT (%) Average value | S.D. | Δ ([CNT % for use of a single drug] − [CNT % for combined use of drugs]) |
|---|---|---|---|---|---|
| 0.05 | Use of a single drug | Not formed | 30.3 | 4.77 | 1.1 |
|  | Combined use of drugs |  | 29.2 | 3.57 |  |
| 0.25 | Use of a single drug | Formed | 33.4 | 4.13 | 4.0 |
|  | Combined use of drugs |  | 29.4 | 1.36 |  |
| 0.5 | Use of a single drug | Formed | 35.7 | 3.97 | 11.5 |
|  | Combined use of drugs |  | 24.2 | 1.09 |  |
| 1.5 | Use of a single drug | Formed | 33.8 | 6.05 | 12.4 |
|  | Combined use of drugs |  | 21.4 | 1.64 |  |

Table 9 shows the calculated CNT results, together with the presence of vascular network formation in the used cell structures.

In the table, "Use of a single drug" shows the results when culture was performed in the presence of oxaliplatin alone, and "Combined use of drugs" shows the results when culture was performed in the presence of both oxaliplatin and bevacizumab. In the "Formation of vascular network" column, "Not formed" indicates that a vascular network structure was not formed, and "Formed" indicates that a vascular network structure was formed.

As a result, in all of the cell structures in which vascular network formation was recognized, except for the cell structures having a HUVEC content of 0.05% in which vascular network formation was not recognized, CNT was markedly lower in the combined use with bevacizumab than in the use of only oxaliplatin. The combined use with bevacizumab significantly increased drug sensitivity, and an effect of combined use was confirmed. It was also confirmed that the effect of combined use was higher in the cell structures with a higher HUVEC content, and that the effect of combined use of the angiogenesis inhibitor and the anti-cancer drug increased in proportional to the number of endothelial cells in the cell structure.

Example 8

The effect of combined use of an antiaogenic agent, bevacizumab, and an anti-cancer drug, oxaliplatin, was assessed using cell structures produced under different conditions for forming a vascular network structure.

The cell culture container, culture media, and bevacizumab used herein were the same as those used in Example 5, and the oxaliplatin used herein was the same as that used in Example 6. Furthermore, HT29 cells were used as the cancer cells.

<Production of Cell Structure>

Cell structures were produced in the same manner as in Example 5, except that HT29 cells were seeded in a Transwell cell culture insert in which a structure formed from NHDF and HUVEC was formed, centrifugation was performed to remove the liquid component, and the culture time in the CO2 incubator (37° C., 5% $CO_2$) was changed to 24, 48, 72, or 96 hours. As a result, the produced cell structures had a vascular network structure for all the culture times.

<Culture in the Presence of Bevacizumab and Oxaliplatin>

The obtained cell structures were cultured in a culture medium in which the amount of bevacizumab added per well of the Transwell cell culture insert was 0 or 2 μg, and the final concentration of oxaliplatin was 100 μg/mL, at 37° C. with 5% $CO_2$ for 72 hours. As a control, the cell structures were cultured in the same manner as described above, except that bevacizumab and oxaliplatin were not added (culture in the absence of the drugs).

<Dispersion of Cell Structure, Viable Cell Count Analysis, and Assessment>

After the cell structures were each dispersed in the same manner as in Example 2, and the obtained dispersions were stained with trypan blue, the number of viable cancer cells was counted to calculate CNT (%). Measurements were repeated three times for each culture condition.

TABLE 10

| Culture time (h) | Drug | Formation of vascular network | CNT (%) Average value | S.D. | Δ ([CNT % for use of a single drug] − [CNT % for combined use of drugs]) |
|---|---|---|---|---|---|
| 24 | Use of a single drug | Formed | 36.0 | 2.13 | 11.3 |
|  | Combined use of drugs |  | 24.7 | 3.23 |  |
| 48 | Use of a single drug | Formed | 36.3 | 1.06 | 12.9 |
|  | Combined use of drugs |  | 23.4 | 3.84 |  |
| 72 | Use of a single drug | Formed | 37.0 | 5.25 | 15.4 |
|  | Combined use of drugs |  | 21.6 | 1.24 |  |
| 96 | Use of a single drug | Formed | 33.8 | 6.05 | 12.4 |
|  | Combined use of drugs |  | 21.4 | 1.64 |  |

Table 10 shows the calculated CNT results, together with the presence of vascular network formation in the used cell structures.

In the table, "Use of a single drug" and "Combined use of drugs", as well as "Not formed" and "Formed" in the "Formation of vascular network" column are the same as those of Table 9.

As a result, the CNT of all the cell structures was markedly lower in the combined use with bevacizumab than in the use of only oxaliplatin. The combined use with bevacizumab significantly increased drug sensitivity, and an effect of combined use was confirmed. It was also confirmed that the effect of combined use was higher as the culture time was longer until the culture time after a cancer cell layer was laminated during production of the cell structure was 72 hours.

Example 9

The anti-cancer effect of an anti-cancer drug, doxorubicin, was assessed using cell structures containing a cell layer containing cancer cells, and a cell layer formed from fibroblasts and vascular endothelial cells, and having a vascular network structure.

The cell structures containing a cell layer containing cancer cells and a cell layer having a vascular network structure used herein were cell structures containing a cell layer in which two types of cells, i.e., NHDF and HUVEC, constituted a multilayer, and a cancer cell layer formed from HT29. The cell culture container, culture media, and anti-cancer drug, doxorubicin, to be assessed used herein were the same as those used in Example 2.

<Preparation of Cell Suspension>

First, $2\times10^6$ NHDF and $3\times10^4$ HUVEC were suspended in a tris-hydrochloric acid buffer containing heparin and collagen (0.1 mg/mL heparin, 0.1 mg/mL collagen, and 50 mM tris; pH: 7.4) to prepare a cancer cell suspension (step (a)). The cell suspension was centrifuged at room temperature at 400×g for 1 minute, the supernatant was removed, and then the cell suspension was resuspended in a suitable amount of culture medium to prepare a stromal cell suspension (steps (a'-1) and (a'-2)).

Separately, $2\times10^4$ HT29 was suspended in a suitable amount of culture medium to prepare a cancer cell suspension (step (a)). The HT29 used was previously fluorescently labeled (product number: PKH67GL, produced by SIGMA).

<Production of Cell Structure 1>

After the stromal cell suspension was seeded in a Transwell cell culture insert (step (b)), the Transwell cell culture insert was centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 24 hours (step (c)).

Subsequently, the cancer cell suspension was seeded in the Transwell cell culture insert in which the structure containing stromal cells was formed (step (b)). Then, the Transwell cell culture insert was centrifuged at room temperature at 400×g for 1 minute to remove the liquid component. After a suitable amount of culture medium was added to the Transwell cell culture insert, culture was carried out in a $CO_2$ incubator (37° C., 5% $CO_2$) for 96 hours (step (c)). After termination of the culture, a cell structure 1 having a cancer cell layer laminated on a stromal cell layer having a vascular network structure (mixed layer (21 layers) of NHDF (20 layers) and HUVEC (1 layer)-HT29 (1 layer)) was obtained.

<Production of Cell Structure 2>

A cell structure 2 was obtained in the same manner as in the cell structure 1, except that a semipermeable membrane with a pore size of 0.4 μm was placed on a structure containing stromal cells, and a cancer cell suspension was seeded on the semipermeable membrane to form a cancer cell layer. Specifically, the obtained cell structure 2 had a cancer cell layer laminated on a stromal cell layer having a vascular network structure through a semipermeable membrane with a pore size of 0.4 μm (mixed layer (21 layers) of NHDF (20 layers) and HUVEC (1 layer)-semipermeable membrane-HT29 (1 layer)). In the cell structure 2, the cells constituting the cancer cell layer were completely separated from the cells constituting the stromal cell layer.

<Production of Cell Structure 3>

A cell structure 3 was obtained in the same manner as in the cell structure 1, except that a cancer cell suspension was first seeded in a Transwell cell culture insert to form a cancer cell layer, a semipermeable membrane with a pore size of 0.4 μm was placed on the cancer cell layer, and a stromal cell suspension was then seeded on the semipermeable membrane to form a stromal cell layer. Specifically, the obtained cell structure 3 had a stromal cell layer having a vascular network structure laminated on a cancer cell layer through a semipermeable membrane with a pore size of 0.4 μm (HT29 (1 layer)-semipermeable membrane-mixed layer (21 layers) of NHDF (20 layers) and HUVEC (1 layer)). In the cell structure 3, the cells constituting the cancer cell layer were completely separated from the cells constituting the stromal cell layer.

<Production of Cell Structure 4>

A cell structure 4 was obtained in the same manner as in the cell structure 2, except that a semipermeable membrane with a pore size of 8 μm was used. Specifically, the obtained cell structure 4 had a cancer cell layer laminated on a stromal cell layer having a vascular network structure through a semipermeable membrane with a pore size of 8 μm (mixed layer (21 layers) of NHDF (20 layers) and HUVEC (1 layer)-semipermeable membrane-HT29 (1 layer)). In the cell structure 4, the cells constituting the cancer cell layer and the cells constituting the stromal cell layer extended to be in contact with each other in the penetration part of the semipermeable membrane.

<Production of Cell Structure 5>

A cell structure 5 was obtained in the same manner as in the cell structure 3, except that a semipermeable membrane with a pore size of 8 μm was used. Specifically, the obtained cell structure 5 had a stromal cell layer having a vascular network structure laminated on a cancer cell layer through a semipermeable membrane with a pore size of 8 μm (HT29 (1 layer)-semipermeable membrane-mixed layer (21 layers) of NHDF (20 layers) and HUVEC (1 layer)). In the cell structure 5, the cells constituting the cancer cell layer and the cells constituting the stromal cell layer extended to be in contact with each other in the penetration part of the semipermeable membrane.

<Culture in the Presence of Doxorubicin>

The obtained cell structures were cultured in a culture medium with a doxorubicin final concentration of 10 μM at 37° C. with 5% $CO_2$ for 72 hours. As a control, the cell structures were cultured in the same manner as described above, except that doxorubicin was not added (culture in the absence of the drug).

<Dispersion of Cell Structure, Viable Cell Count Analysis, and Assessment>

After the cell structures were each dispersed in the same manner as in Example 2, and the obtained dispersions were immersed in a trypan blue solution for trypan blue staining, the number of cells emitting fluorescence and not stained with trypan blue was counted as viable cancer cells. The cell count was performed using a cell counter "Countess II" (produced by Life Technologies) in fluorescence mode.

The CNT (remaining viable cell rate) (%) of each cell structure was calculated based on the following formula, and used as an assessment value.

CNT (%)=[the number of viable cancer cells]/[the number of viable cancer cells in culture in the absence of drug]×100

Table 11 shows the calculated CNT results of each cell structure, together with the number of constituting cells.

Measurements were repeated three times for each culture condition.

TABLE 11

| | CNT (%) | |
|---|---|---|
| Cell structure | Average value | S.D. |
| Cell structure 1 (stromal cell layer - cancer cell layer) | 31.22 | 4.21 |
| Cell structure 2 (stromal cell layer - semipermeable membrane (0.4 μm) - cancer cell layer) | 30.83 | 8.51 |
| Cell structure 3 (cancer cell layer - semipermeable membrane (0.4 μm) - stromal cell layer) | 32.68 | 8.36 |
| Cell structure 4 (stromal cell layer - semipermeable membrane (8 μm) - cancer cell layer) | 31.47 | 1.42 |
| Cell structure 5 (cancer cell layer - semipermeable membrane (8 μm) - stromal cell layer) | 33.03 | 4.12 |

When any cell structure was used, CNT was about 30 to 33%, and doxorubicin sensitivity was high. These results demonstrate that it was possible to assess the anti-cancer effect of doxorubicin even when the stromal cell layer and the cancer cell layer were separated by a semipermeable membrane, as in the case where these layers were not separated. Furthermore, it was confirmed that the pore size of the semipermeable membrane used did not affect assessment, and that drug assessment was possible even when the surface of cancer cells or cancer tissue was not in contact with the cells on the surface of stromal tissue.

Example 10 Case where Cell Structure Formed from Stromal Cells Derived from Lung is Used The effect of combined use of an antiangiogenic agent, bevacizumab, and an anti-cancer drug, 5-FU, was assessed using a cell structure formed from fibroblasts, vascular endothelial cells, and cancer cells, and having a vascular network structure.

The cell structure containing cancer cells and having a vascular network structure used herein was a cell structure in which a cancer cell layer formed from human lung adenocarcinoma cell line A549 (ATCC Number: CCL-185) was laminated on a top surface of a multilayer structure formed from two types of cells, i.e., normal human lung fibroblasts (NHLF) (product number: CC-2512, produced by Lonza) and human dermal microvascular endothelial cells (HMVEC-L) (product number: CC-2527, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The antiangiogenic agent to be assessed was bevacizumab (product number: MAB293, produced by R&D Systems), and the general cytotoxic anti-cancer drug used herein was 5-FU (product number: 064-01403, produced by Wako Pure Chemical Industries, Ltd.).

<Production of Cell Structure>

First, $2 \times 10^6$ NHLF and $1 \times 10^5$ HMVEC-L were suspended in a tris-hydrochloric acid buffer containing heparin and collagen (0.1 mg/mL heparin, 0.1 mg/mL collagen, and 50 mM tris; pH: 7.4) to prepare a cell suspension (the ratio of the number of HMVEC-L to the number of NHLF:5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $2 \times 10^4$ cancer cells suspended in a suitable amount of culture medium was seeded in the Transwell cell culture insert in which the structure was formed (step (b)), the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)). After termination of the culture, a cell structure having a cancer cell layer laminated on a layer having a vascular network structure (mixed layer (21 layers) of NHLF (20 layers) and HMVEC-L (1 layer)-cancer cell (1 layer)) was obtained. The cancer cells used were previously fluorescently labeled (product number: PKH26GL, produced by SIGMA).

<Culture in the Presence of Bevacizumab and 5-FU>

The obtained cell structure was cultured in a culture medium in which the amount of bevacizumab added per well of the Transwell cell culture insert was 0 or 2 μg, and the final concentration of 5-FU was 100 μM, at 37° C. with 5% CO2 for 72 hours. As a control, the cell structure was cultured in the same manner as described above, except that bevacizumab and 5-FU were not added (culture in the absence of the drugs).

<Fixation and Cancer Cell Staining>

The cell structure after culture was dispersed in the same manner as in Example 2, and the dispersed suspension was centrifuged at room temperature at 1120×g for 5 minutes. Thereafter, 400 μL of Fixation/Permilization solution (554722, produced by BD Bioscience) was added for fixation at 4° C. for 30 minutes, and the liquid component was removed. Then, 400 μL of Perm/Wash buffer attached to the kit was added, and centrifugation was performed at room temperature at 1120×g for 5 minutes. Thereafter, a primary antibody Monoclonal Mouse Anti-human Cytokeratin 7 (M7018, produced by DAKO) diluted with 5% FBS-containing PBS was added and allowed to react at 4° C. for 30 minutes. Then, the liquid component was removed, and washing was performed twice using Perm/Wash buffer attached to the kit. A secondary antibody Goat anti-Mouse IgG1 Cross-Adsorbed Secondary Antibody, Alexa Fluor 546 (A-11030, produced by Thermo Fischer Scientific) diluted with 5% FBS-containing PBS was added and allowed to react at 4° C. for 30 minutes. Thereafter, the liquid component was removed, washing was performed twice using Perm/Wash buffer attached to the kit, and the resultant was resuspended in 350 μL of 5% FBS-containing PBS.

<Viable Cell Count Measurement and Assessment>

The number of cells emitting fluorescence in the suspension after fixation and staining was counted as viable cancer cells. The cell count was performed using a flow cytometer (produced by Sony).

Measurements were repeated three times for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

TABLE 12

| A549 | Drug | | CNT (%) | |
|---|---|---|---|---|
| Structure | 5-FU | Bevacizumab | Average value | S.D. |
| 2D | 100 μM | — | 37.7 | 4.5 |
|  | 100 μM | 2 μg | 34.0 | 11.6 |
| 3D | 100 μM | — | 72.9 | 13.0 |
|  | 100 μM | 2 μg | 53.2 | 1.8 |

Table 12 shows the calculated CNT results. As a result, the CNT of the 2D cultures was almost equal between the use of only 5-FU and the combined use with bevacizumab. There was no marked change in drug sensitivity by the combined use with bevacizumab, and an effect of combined use was not confirmed.

In contrast, when the cell structures of the present Example using fibroblasts and vascular endothelial cells derived from the lung were used, CNT was markedly lower in the combined use with bevacizumab than in the use of only 5-FU. The combined use with bevacizumab significantly increased drug sensitivity, and an effect of combined use was confirmed.

Example 11 Effect of Combined Use when Commercially Available Lung Cancer Cell Line is Used The effect of combined use of an antiangiogenic agent, bevacizumab, and an anti-cancer drug, 5-FU, was assessed using a cell structure formed from fibroblasts, vascular endothelial cells, and cancer cells, and having a vascular network structure.

The cell structure containing cancer cells and having a vascular network structure used herein was a cell structure in which a cancer cell layer formed from human lung adenocarcinoma cell line A549 (ATCC Number: CCL-185) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The antiangiogenic agent to be assessed was bevacizumab (product number: MAB293, produced by R&D Systems), and the general cytotoxic anti-cancer drug used herein was 5-FU (product number: 064-01403, produced by Wako Pure Chemical Industries, Ltd.).

<Production of Cell Structure>

First, $2\times10^6$ NHDF and $3\times10^4$ HUVEC were suspended in a tris-hydrochloric acid buffer containing heparin and collagen (0.1 mg/mL heparin, 0.1 mg/mL collagen, and 50 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspension was seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $2\times10^4$ cancer cells suspended in a suitable amount of culture medium was seeded in the Transwell cell culture insert in which the structure was formed (step (b)), the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)). After termination of the culture, a cell structure having a cancer cell layer laminated on a layer having a vascular network structure (mixed layer (21 layers) of NHDF (20 layers) and HUVEC (1 layer)-cancer cell (1 layer)) was obtained. The cancer cells used were previously fluorescently labeled (product number: PKH26GL, produced by SIGMA).

<Culture in the Presence of Bevacizumab and 5-FU>

The obtained cell structures were cultured in a culture medium in which the amount of bevacizumab added per well of the Transwell cell culture insert was 0 or 2 μg, and the final concentration of 5-FU was 100 μm or 1 mM, at 37° C. with 5% $CO_2$ for 72 hours. As a control, the cell structure was cultured in the same manner as described above, except that bevacizumab and 5-FU were not added (culture in the absence of the drugs).

<Fixation and Cancer Cell Staining>

The cell structure after culture was dispersed in the same manner as in Example 2, and the dispersed suspension was centrifuged at room temperature at 1120×g for 5 minutes. Thereafter, 400 μL of Fixation/Permilization solution (554722, produced by BD Bioscience) was added for fixation at 4° C. for 30 minutes, and the liquid component was removed. Then, 400 μL of Perm/Wash buffer attached to the kit was added, and centrifugation was performed at room temperature at 1120×g for 5 minutes. Thereafter, a primary antibody Monoclonal Mouse Anti-human Cytokeratin 7 (M7018, produced by DAKO) diluted with 5% FBS-containing PBS was added and allowed to react at 4° C. for 30 minutes. Then, the liquid component was removed, and washing was performed twice using Perm/Wash buffer attached to the kit. A secondary antibody Goat anti-Mouse IgG1 Cross-Adsorbed Secondary Antibody, Alexa Fluor 546 (A-11030, produced by Thermo Fischer Scientific) diluted with 5% FBS-containing PBS was added and allowed to react at 4° C. for 30 minutes. Thereafter, the liquid component was removed, washing was performed twice using Perm/Wash buffer attached to the kit, and the resultant was resuspended in 350 μL of 5% FBS-containing PBS.

<Viable Cell Count Measurement and Assessment>

The number of cells emitting fluorescence in the suspension after fixation and staining was counted as viable cancer cells. The cell count was performed using a flow cytometer (produced by Sony).

Measurements were repeated three times for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

TABLE 13

| A549 | Drug | | CNT (%) | |
|---|---|---|---|---|
| Structure | 5-FU | Bevacizumab | Average value | S.D. |
| 3D | 100 μM | — | 28.8 | 4.6 |
| | 100 μM | 2 μg | 25.2 | 1.4 |
| | 1 mM | — | 7.7 | 1.8 |
| | 1 mM | 2 μg | 4.8 | 4.0 |

Table 13 shows the calculated CNT results. As a result, for the A549 cells, CNT was also lower in the combined use with bevacizumab than in the use of only 5-FU, regardless of the 5-FU concentration. The combined use with bevacizumab increased drug sensitivity, and an effect of combined use was confirmed. When the 5-FU concentration was 1 mM, CNT was more markedly low, and the combined use with bevacizumab increased drug sensitivity.

Example 12 Case where Commercially Available Lung Cancer Cell Line is Used

The effect of an anti-cancer drug, oxaliplatin, was assessed using a cell structure formed from fibroblasts, vascular endothelial cells, and cancer cells, and having a vascular network structure.

The cell structure containing cancer cells and having a vascular network structure used herein was a cell structure in which a cancer cell layer formed from commercially available lung cancer cell line NCI-H820 (ATCC Number: HTB-181) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The general cytotoxic anti-cancer drug to be assessed was oxaliplatin (produced by Pfizer Inc.).

<Production of Cell Structure>

First, $2\times10^6$ NHDF and $3\times10^4$ HUVEC were suspended in a tris-hydrochloric acid buffer containing heparin and collagen (0.05 mg/mL heparin, 0.05 mg/mL collagen, and 25 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $2\times10^4$ cancer cells suspended in a suitable amount of culture medium was seeded in the Transwell cell culture insert in which the structure was formed, the Transwell cell culture insert was centrifuged at room temperature at 400×g for 1 minute (steps (b'-1) and (b'-2)). After a suitable amount of culture medium was added to the Transwell cell culture insert, culture was carried out in a $CO_2$ incubator (37° C., 5% $CO_2$) for 24 hours (step (c)). After termination of the culture, a cell structure having a cancer cell layer laminated on a layer having a vascular network structure (mixed layer (21 layers) of NHDF (20 layers) and HUVEC (1 layer)-cancer cell (1 layer)) was obtained. The cancer cells used were previously fluorescently labeled (product number: PKH26GL, produced by SIGMA).

<Culture in the Presence of Oxaliplatin>

The obtained cell structure was cultured in a culture medium in which the final concentration of oxaliplatin per well of the Transwell cell culture insert was 1 μg/mL or 10 μg/mL, at 37° C. with 5% $CO_2$ for 72 hours. As a control, the cell structure was cultured in the same manner as described above, except that oxaliplatin was not added (culture in the absence of the drug).

<Dispersion of Cell Structure, Viable Cell Count Analysis, and Assessment>

After the cell structures were each dispersed in the same manner as in Example 2, and the obtained dispersions were immersed in a trypan blue solution for trypan blue staining, the number of cells emitting fluorescence and not stained with trypan blue was counted as viable cancer cells. The cell count was performed using a cell counter "Countess II" (produced by Life Technologies) in fluorescence mode.

Measurements were performed once for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

Table 14 shows the calculated CNT results of each culture. In the table, the "2D" row shows the results of the 2D cultures, and the "3D" row shows the results of the produced cell structures (the cell structures of the present Example).

TABLE 14

| Structure | Drug | CNT (%) |
|---|---|---|
| 2D | 1 μg/mL | 62.9 |
| | 10 μg/mL | 21.0 |
| 3D | 1 μg/mL | 78.2 |
| | 10 μg/mL | 66.7 |

The results confirmed that drug sensitivity was lower, that is, drug resistance was higher, when the cell structures of the present Example were used than when the 2D cultures were used, regardless of the oxaliplatin concentration.

Example 13 Case where Commercially Available Gastric Cancer Cell Line is Used The effect of an anti-cancer drug, oxaliplatin, was assessed using a cell structure formed from fibroblasts, vascular endothelial cells, and cancer cells, and having a vascular network structure.

The cell structure containing cancer cells and having a vascular network structure used herein was a cell structure in which a cancer cell layer formed from commercially available gastric cancer cell line NCI-N87 (ATCC Number: CRL-5822) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The general cytotoxic anti-cancer drug to be assessed was oxaliplatin (produced by Pfizer Inc.).

<Production of Cell Structure>

First, $2\times10^6$ NHDF and $3\times10^4$ HUVEC were suspended in a tris-hydrochloric acid buffer containing heparin and collagen (0.05 mg/mL heparin, 0.05 mg/mL collagen, and 25 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $2\times10^4$ cancer cells suspended in a suitable amount of culture medium was seeded in the Transwell cell culture insert in which the structure was formed (step (b)), the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)). After termination of the culture, a cell structure having a cancer cell layer laminated on a layer having a vascular network structure (mixed layer (21 layers) of NHDF (20 layers) and HUVEC (1 layer)-cancer cell (1 layer)) was obtained. The cancer cells used were previously fluorescently labeled (product number: PKH26GL, produced by SIGMA).

<Culture in the Presence of Oxaliplatin>

The obtained cell structure was cultured in a culture medium in which the final concentration of oxaliplatin per well of the Transwell cell culture insert was 10 μg/mL or 100 μg/mL, at 37° C. with 5% CO2 for 72 hours. As a control, the cell structure was cultured in the same manner as described above, except that oxaliplatin was not added (culture in the absence of the drug).

<Dispersion of Cell Structure, Viable Cell Count Analysis, and Assessment>

After the cell structures were each dispersed in the same manner as in Example 2, and the obtained dispersions were immersed in a trypan blue solution for trypan blue staining, the number of cells emitting fluorescence and not stained with trypan blue was counted as viable cancer cells. The cell count was performed using a cell counter "Countess II" (produced by Life Technologies) in fluorescence mode.

Measurements were performed once for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

Table 15 shows the calculated CNT results of each culture. In the table, the "2D" row shows the results of the 2D cultures, and the "3D" row shows the results of the produced cell structures (the cell structures of the present Example).

TABLE 15

| Structure | Drug | CNT (%) |
|---|---|---|
| 2D | 10 μg/mL | 22.0 |
|  | 100 μg/mL | 10.3 |
| 3D | 10 μg/mL | 45.9 |
|  | 100 μg/mL | 17.7 |

The results confirmed that drug sensitivity was lower, that is, drug resistance was higher, when the cell structures of the present Example were used than when the 2D cultures were used, regardless of the oxaliplatin concentration.

Example 14 Case where Commercially Available Breast Cancer Cell Line is Used The effect of an anti-cancer drug, doxorubicin, was assessed using a cell structure formed from fibroblasts, vascular endothelial cells, and cancer cells, and having a vascular network structure.

The cell structure containing cancer cells and having a vascular network structure used herein was a cell structure in which a cancer cell layer formed from commercially available breast cancer cell line MCF-7 (ATCC Number: HTB-22) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The general cytotoxic anti-cancer drug to be assessed was doxorubicin (product number: 046-21523, produced by Wako Pure Chemical Industries, Ltd.).

<Production of Cell Structure>

First, $2\times10^6$ NHDF and $3\times10^4$ HUVEC were suspended in a tris-hydrochloric acid buffer containing heparin and collagen (0.1 mg/mL heparin, 0.1 mg/mL collagen, and 50 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $2 \times 10^4$ cancer cells suspended in a suitable amount of culture medium was seeded in the Transwell cell culture insert in which the structure was formed (step (b)), the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)). After termination of the culture, a cell structure having a cancer cell layer laminated on a layer having a vascular network structure (mixed layer (21 layers) of NHDF (20 layers) and HUVEC (1 layer)-cancer cell (1 layer)) was obtained. The cancer cells used were previously fluorescently labeled (product number: PKH26GL, produced by SIGMA).

<Culture in the Presence of Doxorubicin>

The obtained cell structure was cultured in a culture medium in which the final concentration of oxaliplatin per well of the Transwell cell culture insert was 1 μM or 10 μM, at 37° C. with 5% $CO_2$ for 72 hours. As a control, the cell structures were cultured in the same manner as described above, except that doxorubicin was not added (culture in the absence of the drug).

<Dispersion of Cell Structure, Viable Cell Count Analysis, and Assessment>

After the cell structures were each dispersed in the same manner as in Example 2, and the obtained dispersions were immersed in a trypan blue solution for trypan blue staining, the number of cells emitting fluorescence and not stained with trypan blue was counted as viable cancer cells. The cell count was performed using a cell counter "Countess II" (produced by Life Technologies) in fluorescence mode.

Measurements were repeated three times for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

Table 16 shows the calculated CNT results of each culture. In the table, the "2D" row shows the results of the 2D cultures, and the "3D" row shows the results of the produced cell structures (the cell structures of the present Example).

TABLE 16

| MCF-7 Structure | Drug Doxorubicin | CNT (%) Average value | S.D. |
|---|---|---|---|
| 2D | 1 μM | 38.9 | 7.5 |
|  | 10 μM | 12.1 | 4.3 |
| 3D | 1 μM | 78.4 | 11.7 |
|  | 10 μM | 48.9 | 8.2 |

The results confirmed that drug sensitivity was lower, that is, drug resistance was higher, when the cell structures of the present Example were used than when the 2D cultures were used, regardless of the doxorubicin concentration.

Example 15 Case where Clinical Breast Cancer Cells are Used

The effect of combined use of an antiangiogenic agent, bevacizumab, and an anti-cancer drug, 5-FU, was assessed using a cell structure formed from fibroblasts, vascular endothelial cells, and cancer cells, and having a vascular network structure.

The cell structure containing cancer cells and having a vascular network structure used herein was a cell structure in which a cancer cell layer formed from patient-derived breast cancer cells CLTH/BC (model number: CL04002-CLTH, produced by Celther) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). The antiangiogenic agent to be assessed was bevacizumab (product number: MAB293, produced by R&D Systems), and the general cytotoxic anti-cancer drug used herein was oxaliplatin (produced by Pfizer Inc.).

<Production of Cell Structure>

First, $2 \times 10^6$ NHDF and $3 \times 10^4$ HUVEC were suspended in a tris-hydrochloric acid buffer containing heparin and collagen (0.1 mg/mL heparin, 0.1 mg/mL collagen, and 50 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $1 \times 10^5$ cancer cells suspended in a suitable amount of culture medium was seeded in the Transwell cell culture insert in which the structure was formed (step (b)), the Transwell cell culture insert was centrifuged at room temperature at 400×g for 1 minute. After a suitable amount of culture medium was added to the Transwell cell culture insert, culture was carried out in a CO2 incubator (37° C., 5% $CO_2$) for 5 hours (step (c)). After termination of the culture, a cell structure having a cancer cell layer laminated on a layer having a vascular network structure (mixed layer (21 layers) of NHDF (20 layers) and HUVEC (1 layer)-cancer cell (1 layer)) was obtained. The cancer cells used were previously fluorescently labeled (product number: PKH26GL, produced by SIGMA).

<Culture in the Presence of Bevacizumab and Oxaliplatin>

The obtained cell structure was cultured in a culture medium in which the amount of bevacizumab added per well of the Transwell cell culture insert was 0 or 2 μg, and the final concentration of oxaliplatin was 10 μg/mL, at 37° C. with 5% $CO_2$ for 72 hours. As a control, the cell structure was cultured in the same manner as described above, except that bevacizumab and oxaliplatin were not added (culture in the absence of the drugs).

<Dispersion of Cell Structure, Viable Cell Count Analysis, and Assessment>

After the cell structures were each dispersed in the same manner as in Example 2, and the obtained dispersions were immersed in a trypan blue solution for trypan blue staining, the number of cells emitting fluorescence and not stained with trypan blue was counted as viable cancer cells. The cell count was performed using a cell counter "Countess II" (produced by Life Technologies) in fluorescence mode.

Measurements were repeated three times for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

TABLE 17

| CLTH/BC Structure | Drug | | CNT (%) | |
| --- | --- | --- | --- | --- |
| | Oxaliplatin | Bevacizumab | Average value | S.D. |
| 3D | 10 μg | — | 69.4 | 8.7 |
| | 10 μg | 2 μg | 53.1 | 6.7 |

Table 17 shows the calculated CNT results. As a result, CNT was markedly lower in the combined use with bevacizumab than in the use of only oxaliplatin. The combined use with bevacizumab significantly increased drug sensitivity, and an effect of combined use was confirmed.

Example 16 Case where KRAS Gene-Mutated Commercially Available Cancer Cell Line is Used An epidermal growth factor receptor tyrosine kinase inhibitor, cetuximab, was assessed using cell structures formed from fibroblasts, vascular endothelial cells, and cancer cells, and having a vascular network structure.

The cell structures containing cancer cells and having a vascular network structure used herein were cell structures in which a cancer cell layer formed from KRAS codon 13 gene-mutated cell line HCT116 (ATCC Number: CCL-247) or KRAS codon 12 gene-mutated cell line A549 (ATCC Number: CCL-185) was laminated on a top surface of a multilayer structure formed from two types of cells, i.e., normal human dermal fibroblasts (NHDF) (product number: CC-2509, produced by Lonza) and human umbilical vein endothelial cells (HUVEC) (product number: CC-2517A, produced by Lonza). The cell culture container used was a Transwell cell culture insert (product number: #3470, produced by Corning), and the culture media used were 10 volume % bovine serum (product number: #35-010-CV, produced by Corning) and 1 volume % penicillin/streptomycin (product number: 168-23191, produced by Wako Pure Chemical Industries, Ltd.)-containing D-MEM (product number: 043-30085, produced by Wako Pure Chemical Industries, Ltd.). Cetuximab (no model number, produced by Merck Serono) was used for assessment.

<Production of Cell Structure>

First, $2 \times 10^6$ NHDF and $3 \times 10^4$ HUVEC were suspended in a tris-hydrochloric acid buffer containing heparin and collagen (0.1 mg/mL heparin, 0.1 mg/mL collagen, and 50 mM tris; pH: 7.4) to prepare a cell suspension (the ratio of the number of HUVEC to the number of NHDF:1.5%) (step (a)). The cell suspensions were each centrifuged at room temperature at 400×g for 1 minute, the supernatant was removed, and then each cell suspension was resuspended in a suitable amount of culture medium (steps (a'-1) and (a'-2)). Subsequently, the cell suspensions were seeded in a Transwell cell culture insert (step (b)), and the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)).

After $2 \times 10^4$ cancer cells suspended in a suitable amount of culture medium was seeded in the Transwell cell culture insert in which the structure was formed (step (b)), the Transwell cell culture insert was centrifuged at room temperature at 400×g for 1 minute. After a suitable amount of culture medium was added to the Transwell cell culture insert, culture was carried out in a $CO_2$ incubator (37° C., 5% $CO_2$) for 24 hours (step (c)). After termination of the culture, a cell structure having a cancer cell layer laminated on a layer having a vascular network structure (mixed layer (21 layers) of NHDF (20 layers) and HUVEC (1 layer)-cancer cell (1 layer)) was obtained. The cancer cells used were previously fluorescently labeled (product number: PKH26GL, produced by SIGMA).

<Culture in the Presence of Cetuximab>

The obtained cell structures were cultured in a culture medium in which the final concentration of cetuximab per well of the Transwell cell culture insert was 100 μg/mL at 37° C. with 5% CO2 for 72 hours. As a control, the cell structures were cultured in the same manner as described above, except that cetuximab was not added (culture in the absence of the drug).

Moreover, for comparison, in place of the above cell structures, structures obtained by culturing cancer cells so as to form a single layer in a general culture container (2D method) were similarly cultured in the presence of cetuximab. A vascular network structure was not confirmed in the 2D cultures obtained by the 2D method.

<Dispersion of Cell Structure, Viable Cell Count Analysis, and Assessment>

After the cell structures were each dispersed in the same manner as in Example 2, and the obtained dispersions were immersed in a trypan blue solution for trypan blue staining, the number of cells emitting fluorescence and not stained with trypan blue was counted as viable cancer cells. The cell count was performed using a cell counter "Countess 11" (produced by Life Technologies) in fluorescence mode.

Measurements were repeated three times for each culture condition.

The CNT (remaining viable cell rate) (%) of each culture was calculated based on the following formula, and used as an assessment value.

CNT (%)=[the number of viable cancer cells]/[the number of viable cancer cells in culture in the absence of drug]×100

The following tables show the calculated CNT results of each culture. In the table, the "2D" row shows the results of the 2D cultures, and the "3D" row shows the results of the produced cell structures (the cell structures of the present Example).

TABLE 18

| HCT116 | Drug | CNT (%) | |
|---|---|---|---|
| Structure | Cetuximab | Average value | S.D. |
| 2D | 100 µg/mL | 97.6 | 9.3 |
| 3D | 100 µg/mL | 100.0 | 16.7 |

TABLE 19

| A549 | Drug | CNT (%) | |
|---|---|---|---|
| Structure | Cetuximab | Average value | S.D. |
| 2D | 100 µg/mL | 96.8 | 7.5 |
| 3D | 100 µg/mL | 103.6 | 6.7 |

Tables 18 and 19 show the calculated CNT results. As a result, for both cancer cell lines, CNT was about 100% when the 2D cultures were used and when the cell structures of the present Example were used. Thus, drug sensitivity was not confirmed. The KRAS codon 13-mutated HCT116 cells and the KRAS codon 12-mutated A549 cells have resistance to cetuximab.

This suggested that when the cell structure according to an embodiment of the present invention was used, it was possible to confirm drug sensitivity that properly reflects the properties of the two cell lines used.

As discussed above, the present application addresses the following; when the drug efficacy of a drug is assessed in an in vitro assessment system, the reliability of the obtained assessment becomes a problem. That is, it is important that the assessment in the assessment system reflects drug efficacy obtained when the drug is actually administered to an organism. In a highly reliable assessment system, the assessment in the in vitro assessment system is highly likely to match the effect obtained by administration into an organism.

The feature of the method disclosed in PTL 1 is that assessment can be performed in an environment close to the concentration of a drug actually administered into an organism. However, considering the culture method, the interaction between the stroma and cancer cells cannot be observed. Moreover, because the stroma cannot be made present, it is hardly said that the actual cancer microenvironment is reproduced. The reliability of the resulting assessment may be low.

An aspect of the present invention is to provide an anti-cancer drug assessment method performed in an in vitro system, whereby more reliable assessment can be performed without using animal models.

Moreover, when the drug efficacy of combination therapy using an antiangiogenic agent is assessed in the drug development stage or the clinical site, in vitro assessment methods, which can be more simply performed, are more preferable than in vivo assessment methods.

Another aspect of the present invention is to provide a method for accurately assessing the drug efficacy of combination therapy with an antiangiogenic agent and an anti-cancer drug using an in vitro system.

In order to solve the above problems, the present inventors conducted extensive research on cell culture methods. As a result, the present inventors found that when an in vivo environment was reproduced in an assessment test of anti-cancer activity, it was possible to reproduce a state in which the assessment object would actually act as in vivo, and to obtain assessment reflecting drug efficacy obtained when the drug was actually administered into an organism. Specifically, the present inventors found that it was possible to obtain more reliable assessment by administering a drug into a structure in which cancer cells were organized while making them coexist with the stroma, such as endothelial cells and fibroblasts, coexisting with cancer cells in the in vivo environment. Thus, the present invention has been produced.

In addition, the present inventors also found that it was also possible to obtain more reliable assessment by allowing an anti-cancer drug to act on cancer cells under conditions close to the in vivo environment in an assessment test of anti-cancer activity, specifically by administering a drug in a state where cancer cells were separated by a semipermeable membrane from a structure in which the cancer cells were organized while making them coexist with the stroma, such as endothelial cells and fibroblasts, coexisting with cancer cells in the in vivo environment. Thus, the present invention has been produced.

The anti-cancer drug assessment method according to the first embodiment of the present invention includes a culture step of culturing a cell structure containing cancer cells and cells that constitute a stroma in the presence of one or more anti-cancer drugs, and an assessment step of assessing the anti-cancer effect of the one or more anti-cancer drugs using, as an indicator, the number of viable cancer cells in the cell structure after the culture step.

In the first embodiment, the cancer cells may be scattered in the cell structure.

In the first embodiment, the cell structure may contain a cell layer containing only cancer cells.

In the first embodiment, in the cell structure, a layer containing the cancer cells and a layer containing the cells that constitute a stroma may be divided by a semipermeable membrane.

In the first embodiment, the semipermeable membrane may have a pore size of 0.4 µm to 8 µm.

In the first embodiment, the cell structure may contain, as the cells that constitute a stroma, one or more members selected from the group consisting of vascular endothelial cells and lymphatic endothelial cells.

In the first embodiment, the cell structure may further contain, as the cells that constitute a stroma, one or more members selected from the group consisting of fibroblasts, nerve cells, dendritic cells, macrophages, and mast cells.

In the first embodiment, the cell structure may contain, as the cells that constitute a stroma, fibroblasts and one or more members selected from the group consisting of vascular endothelial cells and lymphatic endothelial cells, and the total number of vascular endothelial cells and lymphatic endothelial cells in the cell structure may be 0.1% or more of the number of fibroblasts.

In the first embodiment, the cell structure may have a thickness of 5 µm or more.

In the first embodiment, the cell structure may have a vascular network structure.

In the first embodiment, the cell structure may be cultured in the presence of an anti-cancer drug having cytotoxicity and an angiogenesis inhibitor in the culture step, and the anti-cancer effect of combined use of the angiogenesis inhibitor and the anti-cancer drug may be assessed.

In the first embodiment, the cancer cells may be cancer cells obtained from a cancer patient.

In the first embodiment, the culture time in the culture step may be 24 to 96 hours.

The anti-cancer drug assessment kit according to the second embodiment of the present invention is a kit for preforming the anti-cancer drug assessment method according to the first embodiment, and contains a cell structure containing at least cells that constitute a stroma, and includes a cell culture container for accommodating the cell structure.

In the second embodiment, the cell structure may contain a semipermeable membrane on a top surface thereof.

In the second embodiment, the cell structure may have a vascular network structure.

In the second embodiment, the cell structure may have a thickness of 5 μm or more.

In the anti-cancer drug assessment method according to the first embodiment of the present invention, the drug efficacy of an anti-cancer drug is assessed using, as an indicator, the influence thereof on cancer cells contained in a cell structure containing a stroma closer to the in vivo state, or cancer cells separated from the cell structure containing a stroma by a semipermeable membrane. Therefore, highly reliable assessment can be obtained even in an in vitro assessment system.

Moreover, the above assessment method can be performed more simply using the anti-cancer drug assessment kit according to the second embodiment of the present invention.

Obviously, numerous modifications and variations of the present invention are possible in light of the above teachings. It is therefore to be understood that within the scope of the appended claims, the invention may be practiced otherwise than as specifically described herein.

What is claimed is:

1. A method of assessing an anti-cancer drug, comprising:
   culturing a cell structure comprising cancer cells and stromal cells in a presence of at least one anti-cancer drug; and
   assessing an anti-cancer effect of the at least one anti-cancer drug based on a number of viable cancer cells in the cell structure after the culturing,
   wherein the stromal cells comprises a first type of stromal cells and a second type of stromal cells such that the first type of stromal cells comprises endothelial cells and forms a vascular network structure in the cell structure and that the second type of stromal cells is stromal cells other than the endothelial cells.

2. The method of claim 1, wherein the cancer cells are scattered in the cell structure.

3. The method of claim 1, wherein the cell structure comprises a cell layer including only the cancer cells.

4. The method of claim 1, wherein the cell structure includes a semipermeable membrane that divides a layer including the cancer cells and a layer including the stromal cells.

5. The method of claim 4, wherein the semipermeable membrane has a pore size of 0.4 μm to 8 μm.

6. The method of claim 1, wherein the first type of stromal cells includes at least one selected from the group consisting of vascular endothelial cells and lymphatic endothelial cells.

7. The method of claim 6, wherein the second type of stromal cells includes at least one selected from the group consisting of fibroblasts, nerve cells, dendritic cells, macrophages, and mast cells.

8. The method of claim 1, wherein the stromal cells comprise the second type of stromal cells comprising fibroblasts and the first type of stromal cells comprising at least one selected from the group consisting of vascular endothelial cells and lymphatic endothelial cells such that a total number of the vascular endothelial cells and the lymphatic endothelial cells in the cell structure is 0.1% or more of a number of the fibroblasts.

9. The method of claim 1, wherein the cell structure has a thickness of 5 μm or more.

10. The method of claim 1, wherein the cell structure has the vascular network structure having at least one of a vascular network structure of blood vessels and a vascular network structure of lymph vessels.

11. The method of claim 10, wherein the culturing comprises culturing the cell structure in the presence of the anti-cancer drug having cytotoxicity and an angiogenesis inhibitor, and the assessing comprises assessing the anti-cancer effect of a combined use of the angiogenesis inhibitor and the anti-cancer drug with respect to a single use of the anti-cancer drug.

12. The method of claim 1, wherein the cancer cells are cancer cells from a cancer patient.

13. The method of claim 1, wherein the culturing is conducted for 24 to 96 hours.

14. The method of claim 1, wherein the stromal cells comprise the first type of stromal cells and the second type of stromal cells such that a total number of the endothelial cells in the cell structure is sufficient to form the vascular network structure in the cell structure.

15. The method of claim 1, wherein the culturing comprises culturing the cell structure in the presence of the anti-cancer drug having cytotoxicity and an angiogenesis inhibitor, and the assessing comprises assessing the anti-cancer effect of a combined use of the angiogenesis inhibitor and the anti-cancer drug with respect to a single use of the anti-cancer drug.

16. The method of claim 1, wherein the stromal cells comprise the second type of stromal cells comprising fibroblasts and the first type of stromal cells comprising at least one selected from the group consisting of vascular endothelial cells and lymphatic endothelial cells such that a total number of the vascular endothelial cells and the lymphatic endothelial cells in the cell structure is in a range of 0.1% to 10% of a number of the fibroblasts.

17. The method of claim 8, wherein the cell structure has the vascular network structure having at least one of a vascular network structure of blood vessels and a vascular network structure of lymph vessels.

18. The method of claim 17, wherein the culturing comprises culturing the cell structure in the presence of the anti-cancer drug having cytotoxicity and an angiogenesis inhibitor, and the assessing comprises assessing the anti-cancer effect of a combined use of the angiogenesis inhibitor and the anti-cancer drug with respect to a single use of the anti-cancer drug.

19. The method of claim 16, wherein the cell structure has the vascular network structure having at least one of a vascular network structure of blood vessels and a vascular network structure of lymph vessels.

20. The method of claim 19, wherein the culturing comprises culturing the cell structure in the presence of the anti-cancer drug having cytotoxicity and an angiogenesis inhibitor, and the assessing comprises assessing the anti-cancer effect of a combined use of the angiogenesis inhibitor and the anti-cancer drug with respect to a single use of the anti-cancer drug.

* * * * *